United States Patent [19]
Hance et al.

[11] Patent Number: 5,877,273
[45] Date of Patent: Mar. 2, 1999

[54] PEPTIDES ENCODED BY NUCLEASE SEQUENCES OF ACTINOMYCETALES AND APPLICATION AS IMMUNOGENIC COMPOSITIONS

[75] Inventors: Allan Johnson Hance; Bernard Grandchamp-Desraux; Veronique Levy-Frebault; Brigitte Gicquel, all of Paris, France

[73] Assignee: Institut National de la Sante et de la Recherche Mediale-Inserm & Institute Pasteur, Paris, France

[21] Appl. No.: 473,020

[22] Filed: Jun. 6, 1995

Related U.S. Application Data

[62] Division of Ser. No. 623,729, filed as PCT/FR90/00274 Apr. 13, 1990.

[30] Foreign Application Priority Data

Apr. 17, 1989 [FR] France ................................ 89-05057

[51] Int. Cl.[6] ............................ A61K 38/00; C07K 16/00
[52] U.S. Cl. ....................................... 530/300; 530/387.1
[58] Field of Search ................................. 530/300, 387.1

[56] References Cited

U.S. PATENT DOCUMENTS 4,358,535  11/1982  Falkow et al. ............................... 435/5

FOREIGN PATENT DOCUMENTS

| 0200362 | 12/1986 | European Pat. Off. |
| 0288306 | 10/1988 | European Pat. Off. |
| WO 8800974 | 2/1988 | WIPO |
| WO 8805823 | 8/1988 | WIPO |
| WO 8806591 | 9/1988 | WIPO |

OTHER PUBLICATIONS

Pao, C.C., et al., "The Detection of Mycobacterial DNA Sequences in Uncultured Clinical Specimens with Cloned Mycobacterium Tuberculosis DNA as Probes," *Tubercle*, 69(1):27–36 (Mar. 1988).

Picken, R.N., et al., "DNA Probes for Mycobacteria. I. Isolation of DNA Probes for the Identification of Mycobacterium Tuberculosis Complex and for Mycobacteria other than Tuberculosis (MOTT)," *Molecular and Cellular Probes*, 2:111–124 (1988).

Hance, A.J. et al., "Detection and Identification of Mycobacteria by Amplification of Mycobacterial DNA," *Molecular Microbiology*, 3(7):843–849 (1989).

Plikaytis, B.B. et al., "Rapid Sensitive and Specific Detection of Mycobacteria Using Gene Amplification Techniques," *Abstracts of the Annual Meeting of the American Society for Microbiology*, 89(0):162 (1989) Abstract No. U–43.

*Primary Examiner*—Ardin H. Marschel
*Assistant Examiner*—Jezian Riley
*Attorney, Agent, or Firm*—Walter H. Dreger; Jan P. Brunelle

[57] ABSTRACT

The present invention relates to nucleotide sequences of Actinomycetales, in particular of mycobacteria, to oligonucleotides contained within said nucleotide sequences, to their uses as primers for the synthesis of Actinomycetales DNA and as probes for the detection of DNA and/or the transcription products of Actinomycetales, in particular of mycobacteria, to the products of expression of said sequences, to their uses and to antibodies directed towards the said products, to a method for detecting and identifying Actinomycetales and its uses, as well as to immunogenic compositions comprising the said expression products.

27 Claims, 9 Drawing Sheets

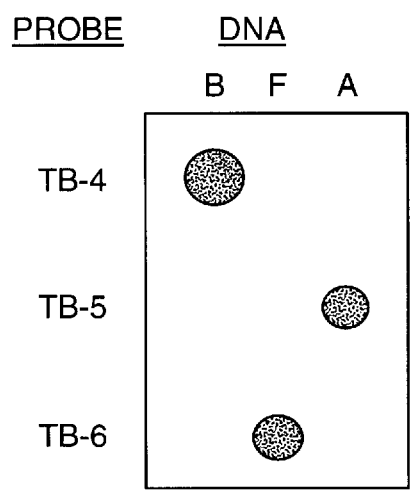
FIG._1

```
                    TYR GLU LYS ILE GLY ALA GLU LEU VAL LYS GLU VAL ALA LYS LYS THR ASP ASP VAL ALA GLY
                  G TAC GAG AAG ATC GGC GCC GAG CTG GTC AAA GAG GTA GCC AAG AAG ACC GAT GAC GTC GCC GGT
M. bovis BCG        ASP GLY THR THR THR ALA THR VAL LEU
                    GAC GGC ACC ACG ACG GCC ACC GTG CTG
M. avium          - --- --- --- --- --- --- --- --- --- --G --A --C --- --- --- --- --C --- --- --- ---
                    --- --- --G --- --- --- --G --- --C
M. para-          - --- --- --- --- --- --- --- --- --- --G --A --C --- --- --- --- --C --- --- --- ---
tuberculosis        --- --- --G --- --- --- --G --- --C
M. fortuitum      - --- --- --- --- --- --T --- --C --- --G --A --C --- --- --- --- --C --- --- --G --C
                  1 --- --- --- --C --C --- --- --T ---                    50

M. bovis BCG        ALA GLN ALA LEU VAL ARG GLU GLY LEU ARG ASN VAL ALA ALA GLY ALA ASN PRO LEU GLY LEU
                    GCC CAG GCG TTG GTT CGC GAG GGC CTG CGC AAC GTC GCG GCC GGC GCC AAC CCG CTC GGT CTC
                    LYS ARG GLY ILE GLU LYS ALA VAL GLU
                    AAA CGC GGC ATC GAA AAG GCC GTG GAG
M. avium            --- --- --- --- --C --- --- --- --- --- --- --- --- --- --- --- --- --- --G --- ---
                    --G --- --- --- --G --- --- --C ---
M. para-            --- --- --- --- --C --- --- --- --- --- --- --- --- --- --- --- --- --- --G --- ---
tuberculosis        --G --- --- --- --G --- --- --C ---
M. fortuitum        --A --- --C C-- --- --T --A --T --- --- --- --- --T --- --- --- --- --- --- --C --G
                    --G --- 100 --- --G --- --- --C ---                                      150
```

FIG._2A

```
                  LYS VAL THR GLU THR LEU LEU LYS GLY ALA LYS GLU VAL GLU THR LYS GLU GLN ILE ALA ALA
                  AAG GTC ACC GAG ACC CTC CTC AAG GGC GCC AAG GAG GTC GAG ACC AAG GAG CAG ATT GCG GCC
M. bovis BCG      THR ALA ALA ILE SER ALA GLY ASP GLN
                  ACC GCA GCG ATT TCG GCG GGT GAC CAG
                                                  SER                                     ASP
M. avium          --- --- --- --- --- --- --- --- TCG --- --- --- --- --- --- --- --C --- --C --T ---
                  --- --G --C --C --C --- --C --- ---

SER                                     ASP
M. para-          --- --- --- --- --- --- --- --- TCG --- --- --- --- --- --- --- --C --- --C --T ---
tuberculosis      --- --G --C --C --C --- --C --- ---

SER
M. fortuitum      --- --- --- --- --G --- --G --- A-- --- --- --- --G --- --- --- --- --- --C --T ---
                          GLY             200
                  --- --C -GT --C --C --C --- --- ---
                      250

SER ILE GLY ASP LEU ILE ALA GLU ALA MET ASP LYS VAL GLY ASN GLU GLY VAL ILE THR VAL
                  TCC ATC GGT GAC CTG ATC GCC GAG GCG ATG GAC AAG GTG GGC AAC GAG GGC GTC ATC ACC GTC
M. bovis BCG      GLU GLU SER
                  GAG GAG TCC
M. avium          --G --- --C --- --- --- --- --- --- --- --- --- --C --- --- --- --- --- --- --- ---
                  --- --- ---

M. para-          --G --- --C --- --- --- --- --- --- --- --- --- --C --- --- --- --- --- --- --- ---
tuberculosis      --- --- ---

M. fortuitum      --- --- --- --- --- --- --- --- --C --- --- --- --C --- --- --- --T --- --- --- ---
                                                     300
                  --- --- AG-
                          343
```

FIG._2B

```
         10         20         30         40         50         60         70         80         90        100
TACGAGAAGATCGGCGCCGAGCTGGTCAAGGAAGTCGCCAAGAAGACCGACGACGTCGCCGGTGACGGACGACGGCCACGGTGCTCGCCCAGGCGT
         ^          ^   ^                         ^           ^                                ^     ^     ^
      MBOII  AHAII ALUI                        MBOII    TTHIIII    HAPII                     EAEI BSPI286 ECORII
      SAU3A                                             AATII      HPHI                    HAEIII HGIAI  SCRFI
         BANI                                           AHAII      MAEIII
         HAEIII
         NARI
         CFOI 110        120        130        140        150        160        170        180        190        200
TGGTCCGCGAGGGCCTGCGCAACGTCGCGGCCGCCAACCCCGCTGGGTCTCAAGCGCGGCCATCGAGAAGGCCGTCGAGAAGGTCACCGAGACCCTGCT
    ^  ^    ^  ^^^^^^                              ^^^                         ^         ^^
 AFLI  MNLI  AOSI  ACCII  AHAII                CFOI SFANI                   HAEIII    BSTEII
 SAU96A SAU96A    FNU4HI CFOI                  ACCII TAQI                    TAQI     MAEIII
        ACCII HAEIII    EAEI BANI                   FNU4HI                            HPHI
              CFOI     XMAIII BSTXI
                       HAEIII
                       NAEI
                       HAPII
                       HAEIII
                       NARI 210        220        230        240        250        260        270        280        290        300
CAAGTCGGCCAAGGAGGTCGAGAGACCAAGGACCAGATCGCTGCCACCGGCGCCATCTCCGCGGGCGACCAGTCGATCGGCGACCTGATCGGCCGAGGCGATG
     ^  ^      ^   ^  ^    ^^^^^            ^^                ^^                         ^     ^         ^
  EAEI MNLI   STYI SAU3A AFLI BGLI ACCII              SACII              TAQI SAU3A  MNLI
 HAEIII TAQI       BBVI SACII                         ACCII              PVUI
  STYI              AFLI FNU4HI                                          SAU3A
                    SAU96A   FNU4HI
                             EAEI
                             HAEIII 310        320        330        340
GACAAGGTCGGCAACGAGGGCGTCATCACCGTCGAGGAGTCC
 ^       ^     ^     ^
 TTHIIII MNLI  HPHI  TAQI HINFI
         AHAII       MNLI
         HGAI
```

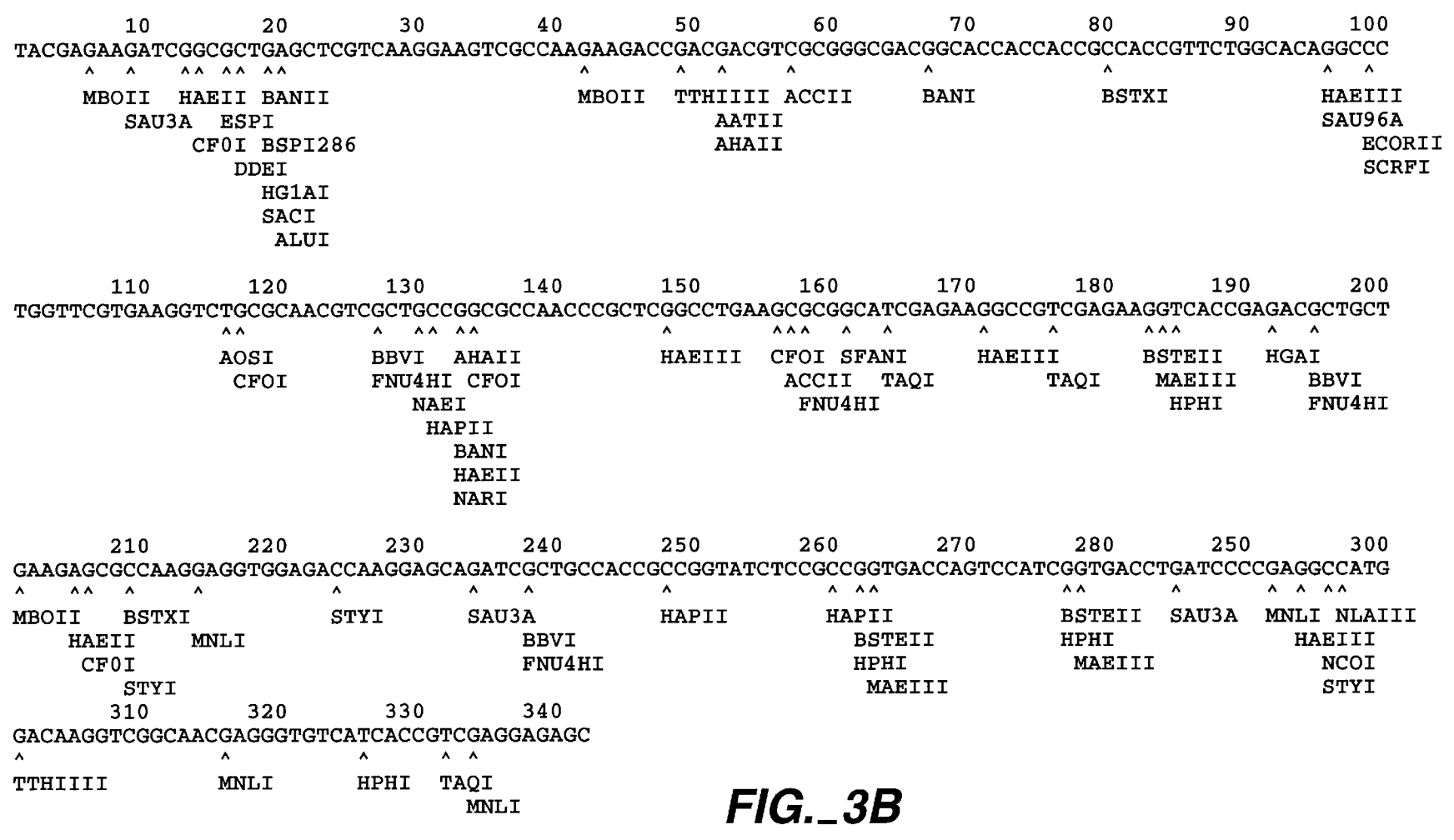

```
          10        20        30        40        50        60        70        80        90       100
TACGAGAAGATCGGGCGCCGAGCTGGTCAAGGAAGTCGCCAAGAAGACCGACGAGACGTCGCCGGTGACGGCCACGACGACGGCCACGGTGCTCGCCCAGGCGT
           ^       ^^                           ^        ^        ^                     ^     ^  ^     ^
          MBOII  AHAII ALUI                   MBOII   TTHIIII   HAPII                   EAEI  BSPI286 ECORII
                 SAU3A                                 AATII    HPHI                         HAEIII HGIAI SCRFI
                 BANI                                  AHAII   MAEIII
                 HAEIII
                 NARI
                 CFOI 110       120       130       140       150       160       170       180       190       200
TGGTCCCGCCGAGGGCCTGCGCAACGTCGCCGGCCGCCAACCCGCTGGGTCTCAAGCGCATCGAGAAGGCCGTCGAGAAGTCACCGAGACCCTGCT
 ^        ^^        ^^^^^^           ^             ^^^^^    ^                ^^        ^
AFLI    MNLI  AOSI  ACCII AHAII                  CFOI SFANI HAEIII        BSTEII
SAU96A  SAU96A      FNU4HI CFOI                  ACCII TAQI TAQI         MAEIII
ACCII   HAEIII      EAEI BANI                    FNU4HI                  HPHI
        CFOI        XMAIII BSTXI
                    HAEIII
                    NAEI
                    HAPII
                    HAEIII
                    NARI 210       220       230       240       250       260       270       280       290       300
CAAGTCGGCCAAGGAGGTCGAGACCAAGGACCAGATCGCTGCCACCGCGGCCATCTCCGCGGCCAGTCGATCGGCGACCTGATCGCCGAGGCGATG
 ^^        ^      ^    ^    ^^   ^^^^                  ^^         ^   ^           ^^^                     ^
EAEI     MNLI   STYI  SAU3A BGLI ACCII              SACII        TAQI           SAU3A              MNLI
HAEIII   TAQI   AFLI  BBVI  SACI1 FNU4HI            ACCII        PVUI
STYI            SAU96A FNU4HI     EAEI                           SAU3A
                                  HAEIII 310       320       330       340
GACAAGGTCGGCAACGAGGGCGTCATCACCGTCGAGGAGTCC
 ^        ^^        ^   ^
TTHIIII  MNLI     HPHI TAQI HINFI
         AHAII         MNLI
         HGAI
```

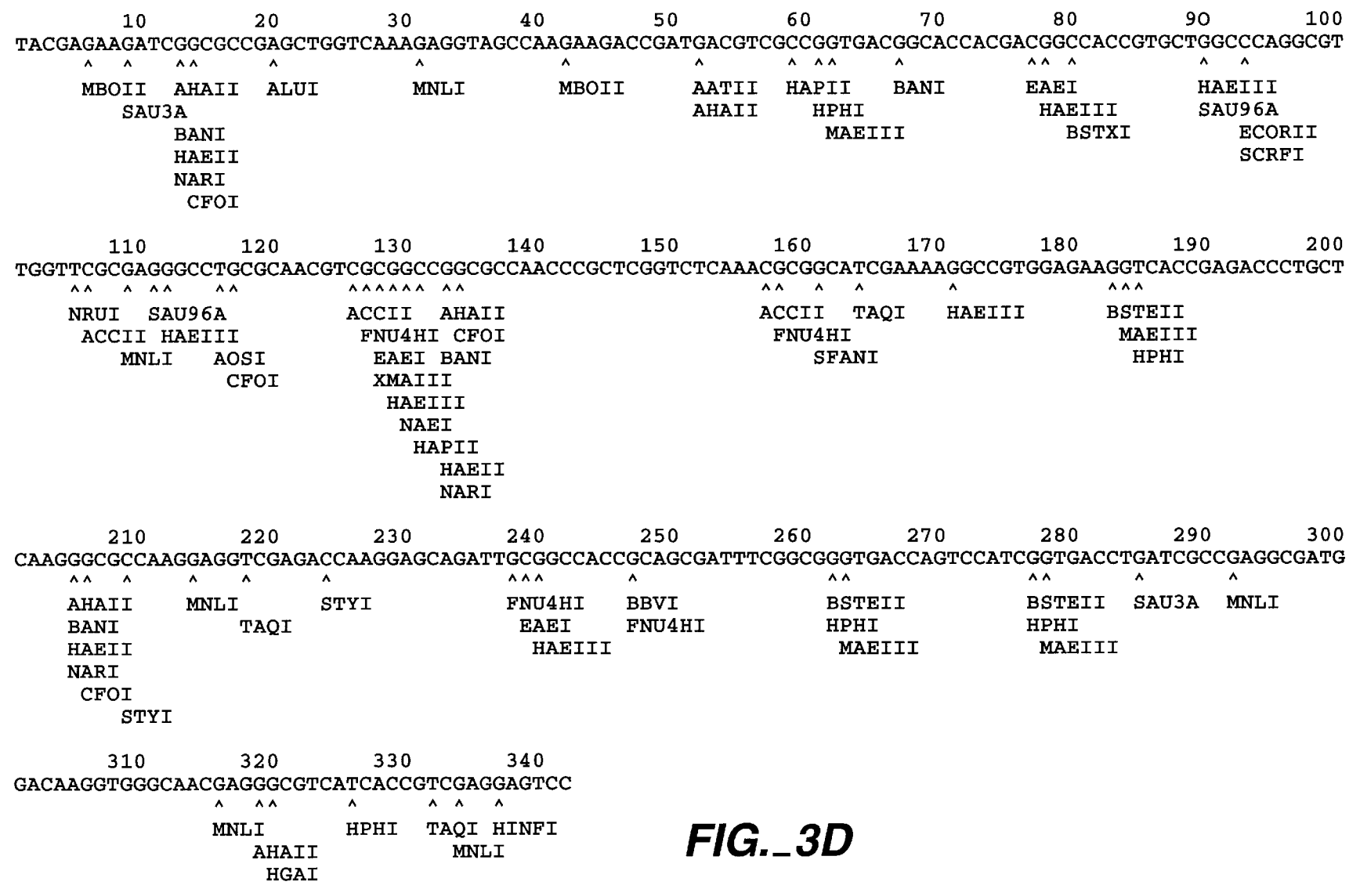

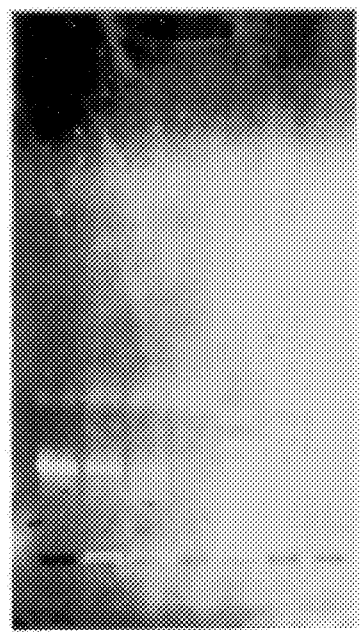
FIG._4A
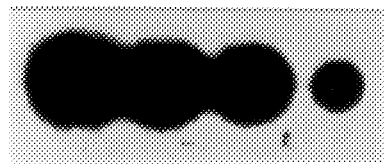
FIG._4B

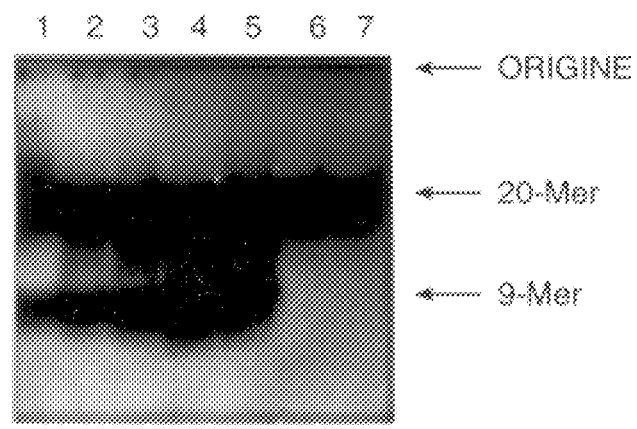
FIG._5
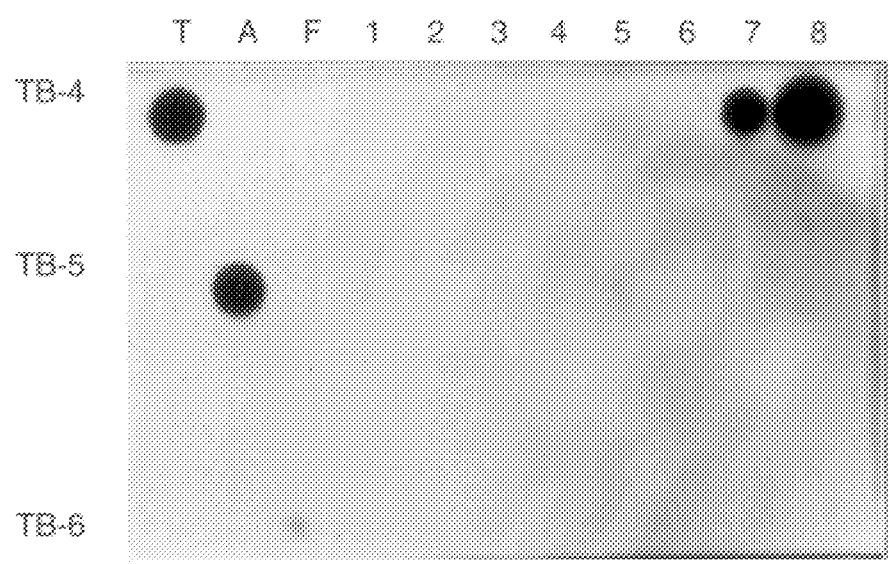
FIG._6

PEPTIDES ENCODED BY NUCLEASE SEQUENCES OF ACTINOMYCETALES AND APPLICATION AS IMMUNOGENIC COMPOSITIONS

CROSS-REFERENCE TO RELATED APPLICATION

This is a division of application Ser. No. 07/623,729, filed as PCT/FR90/00274, Apr. 13, 1990.

FIELD OF THE INVENTION

The present invention relates to nucleotide sequences of Actinomycetales, in particular of mycobacteria, to oligonucleotides contained within the said sequences, to their uses as primers for the synthesis of Actinomycetales DNA and as probes for the detection of DNA and/or of the transcription products of Actinomycetales, in particular of mycobacteria, to the products of expression of the said sequences, to their uses and to antibodies directed towards the said products, to a method for detecting and identifying Actinomycetales and its uses, as well as to immunogenic compositions comprising the said expression products.

BACKGROUND OF THE INVENTION

Tuberculosis and leprosy are known to be major public health problems. They are currently approximately $60 \times 10^6$ individuals suffering from tuberculosis in the world (with an annual mortality of $3 \times 10^6$), and approximately $15 \times 10^6$ individuals suffering from leprosy. In France, approximately $10^4$ new cases of tuberculosis appear every year. Vaccination with BCG (Bacillus Calmette-Guérin, an attenuated strain of M. bovis) is far from effective in all populations. This efficacy varies approximately from 80% in Western countries such as England to 0% in India (results of the latest vaccination trial in Chingleput). The appearance of strains of M. tuberculosis resistant to the usual antituberculosis agents and the existence of mycobacterioses due to other, increasingly common mycobacteria such as M. avium, especially in patients with immunosuppression (AIDS in the largest number of cases), add to the urgency of developing a rapid method of detecting and identifying mycobacteria.

The diagnosis of tuberculosis and other related mycobacterioses is difficult to carry out; in effect the microorganisms responsible for these diseases are often present in small amounts, and when the amount of them is detectable by the methods conventionally used, the disease is already progressing and the patients are contagious to those around them. As a result of the very long generation time of these bacteria (24 h for M. tuberculosis compared with 20 min for E. coli), culturing these organisms is difficult. Thus, it requires 6 to 8 weeks to identify the microorganisms, and longer to obtain an antibiogram usable for appropriate treatment of the patients. The need for a detection test not requiring culturing of the microorganisms, and directly usable with the pathological samples even when the microorganisms are present therein at low concentrations, is hence essential.

Several techniques are currently used in clinical practice for identifying a mycobacterial infection.

In the first place, direct detection of the microorganisms in the microscope should be mentioned; this technique is rapid, but does not permit identification of the mycobacterial species observed, and lacks sensitivity in as much as a large number of microorganisms have to be present in the sample ($>10^4$/ml) in order to permit reliable detection (BATES J., CHEST, 1979, 76, (suppl.), 757–763).

Cultures, when positive, have a specificity approaching 100%, and permit identification of the mycobacterial species isolated; nevertheless, as specified above, growth of mycobacteria in vitro can be achieved only in the space of 3 to 6 weeks, and when few mycobacteria are present at the site of infection, repeated culturing is necessary in order to ensure a positive result (BATES J., 1979 and BATES J. et al., Am. Rev. Respir. Dis., 1986, 134, 415–417).

Serological techniques can prove useful under some conditions, but their use is limited by their low sensitivity and/or their low specificity (DANIEL T. M. et al., Am. Rev. Respir. Dis., 1987, 135, 1137–1151).

The presence or absence of mycobacteria may also be determined by hybridisation with DNA or RNA using probes specific for DNA sequences (KIEHN T. E. et al., J. Clin. Microbiol., 1987, 25, 1551–1552; ROBERTS M. C. et al., J. Clin. Microbiol., 1987, 25, 1239–1243; DRAKE T. A. et al., J. Clin. Microbiol., 1987, 25, 1442–1445). However, these methods also require culturing of the microorganisms.

Some DNA sequences of various mycobacteria, and in particular some genes coding for mycobacterial antigens have been described. There may be mentioned, in particular, PCT International Application WO 88/00,974, whose inventor is YOUNG R. and the content of which is recapitulated in a paper published in Nature, 1985, 316, 450; these publications describe the genes coding for five immunodominant antigens of M. leprae and, in particular, the gene coding for the 65-kD antigen has been sequenced. There may also be mentioned PCT International Application WO 88/05,823, whose co-inventors are HUSSON R., YOUNG R. and SHINNICK T. and the content of which is recapitulated in the paper published in J. Bact., 1987, 169, 1080–1088 and which describes the genes of M. tuberculosis coding for protein antigens, and in particular for the 65-kD antigen. This International Application specifies, in particular, that the genes of M. tuberculosis coding for five immunologically active proteins were isolated by systematic screening of a recombinant DNA library expressed in a bacteriophage lambda gt11, with a collection of monoclonal antibodies directed towards the protein antigens of this bacterium. One of the antigens of M. tuberculosis, a 65-kD protein possesses determinants commonn to M. tuberculosis and M. leprae.

PCT International Application WO 88/06,591, a co-inventor of which is, in particular, T. SHINNICK, describes a recombinant protein of 540 amino acids (65-kD protein) and also the DNA sequence and the vectors for the expression of the said protein, as well as the uses of the said recombinant protein. This Application also describes peptides corresponding to sequences of this protein and their uses.

Genes coding for proteins of other mycobacteria (M. africanum, M. smegmatis, M. bovis BCG and M. avium) have also been isolated. There may be mentioned, in particular, THOLE et al. (Infect. Immunol., 1987, 55, 1466–1475), who have described a 64-kD protein of M. bovis BCG expressed in E. coli.

However, the amounts of mycobacterial DNA present in most biological samples are insufficient to give a positive signal; this technique has hence proved unsuitable for the identification of mycobacterial DNA extracted directly from biological samples.

A number of studies have also shown some degree of structural homology between the different mycobacteria. However, differences in the DNA sequence of M. tuberculosis and M. bovis have been described in the 3' region of the open reading frame of the 65-kD antigen (SHINNICK et al., 1987, THOLE et al., 1987), but a homologous region has not been observed in the DNA of M. leprae (MEHRA et al., Proc. Nat. Acad. Sci. U.S.A., 1986, 83, 7013–7017, also PCT 88/000,974).

There are also publications which describe vaccines against mycobacteria, produced by genetic engineering; there may be mentioned, in particular, PCT International Application WO 88/02,027, which describes recombinant poxviruses capable of expressing mycobacterial antigens and which enable a protective immunological response to mycobacteria to be obtained.

The various detection methods of the prior art do not permit, on the one hand the detection and rapid identification of an Actinomycetales infection directly from a biological sample, and on the other hand the specific identification of groups, species or strains, which may even be present in small amounts.

The additional references which follow also constitute the state of the art prior to the present invention.

BAESS I., Acta Path. Microbiol. Scand., 1979, 87, 221–226; BEAUCAGE S. L. et al., Tetrahedron Lett., 1981, 22, 1859–1862; EISENACH K. D. et al., Am. Rev. Respir. Dis., 1986, 133, 1065–1068; GHEORGHIU M. et al., J. Biol. Standardization, 1988, 16, 15–26; GLASSROTH J. et al., N. Engl. J. Med., 1980, 302, 1441–1450; HAWKINS C. C. et al., Ann. Intern. Med., 1985, 105, 184–188; IMAEDA T., Int. J. Systematic Bacteriol., 1985, 35, 147–150; IMAEDA T. et al., Int. J. Systematic Bacteriol., 1988, 38, 151–156; KOGAN S. C. et al., N. Engl. J. Med., 1987, 317, 985–990; LI H. et al., Nature (Lond.), 1988, 335, 414–417; LU M. C. et al., Infect. Immun., 1987, 55, 2378–2382; MANIATIS T. et al., 1982, Cold Spring Harbor, N.Y.; McFADDEN J. J. et al., Mol. Microbiol., 1987, 1, 283–291; PAO C. C. et al., Tubercle, 1988, 69, 27–36; PATEL R., J. Gen. Microbiol., 1986, 132, 541–551; SAIKI R. K. et al., Science, 1988, 239, 487–491; SANGER F. et al., Proc. Natl. Acad. Sci. U.S.A., 1977, 74, 5463–5467; SMIDA J. et al., Int. J. Leprosy, 1988, 56, 449–454; THEIN S. L. et al., in Human Genetic Diseases, 1986, IRL Press, 33–50; THOLE J. E. R. et al., Infect. Immun., 1985, 50, 800–806; WATSON E. A., Canad. J. Pub. Health, 1935, 26, 268–275; WOLINSKY E., Am. Rev. Respir. Dis, 1979, 119, 107–159.

SUMMARY OF THE INVENTION

The aim of the present invention is accordingly to provide a detection and identification method enabling small amounts of DNA extracted from microorganisms, themselves present in limited numbers, to be detected, the method being rapid and enabling Actinomycetales infection, and in particular a mycobacterial infection, a Nocardia infection or a Rhodococcus infection, to be identified directly in pathological samples without having to carry out culturing.

BRIEF DESCRIPTION OF THE DRAWINGS

FIG. 1 shows the hybridization of amplified DNA of M. bovis (B), M. avium (A) and M. fortuitum (F) with the specific probes TB4 (SEQ ID NO:12), TB-5 (SEQ ID NO:13) and TB-6 (SEQ ID NO:14), respectively.

FIG. 2 shows the DNA sequences of the amplified fragments obtained from the gene coding for the 65 kD antigen of M. bovis, M. avium, M. paratuberculosis and M. fortuitum.

FIGS. 3a–3d show a number of restriction sites of the fragments of 343 nucleotides contained within the gene encoding the 65 kD antigen of M. avium (FIG. 3a), M. fortuitum (FIG. 3b), M. paratuberculosis (FIG. 3c) and M. bovis (FIG. 3d).

FIGS. 4a and 4b show a gel and a dot blot, respectively, demonstrating results for the detection assay for DNA extracted from samples containing $10^6$ human mononuclear blood cells and $6\times10^5$ (column 1), $6\times10^4$ (column 2), $6\times10^3$ (column 3), 600 (column 4), 60 (column 5) and 6 (column 6) M. bovis bacilli, and amplified using Taq polymerase and the oligonucleotide primers TB-1 (SEQ ID NO:9) and TB-2 (SEQ ID NO:10).

FIG. 5 shows the detection of amplified mycobacterial DNA sequences by the oligonucleotide restriction test wherein purified mycobacterial DNA is amplified and equivalent amounts of the amplified product from M. avium (columns 1–5), M. bovis BCG (column 6) and M. fortuitum (column 7) are evaluated.

FIG. 6 shows the results from the analysis of mycobacterial DNA in a sputum specimen wherein DNA purified from M. tuberculosis (T), M. avium (A) and from M. fortuitum (F) and DNA extracted from sputum samples which yielded a negative culture (columns 1–6) or a positive culture for M. tuberculosis (columns 7 and 8) was amplified using Taq polymerase in the case of PCR or using another polymerase and the oligonucleotides TB-1 (SEQ ID NO:9) and TB-2 (SEQ ID NO:10).

DESCRIPTION OF THE PREFERRED EMBODIMENTS

The subject of the present invention is a nucleotide sequence derived from Actinomycetales, characterised in that it consists of a homologous sequence of a gene common to Actinomycetales chosen from the group comprising mycobacteria, Nocardia and Rhodococcus, within which sequence there are conserved regions and variable regions, and in that it comprises between 250 and 500 base pairs.

Nucleotide sequence is understood, in the present invention, to mean both a double-stranded DNA sequence, a single-stranded DNA sequence and the products of transcription of the said DNA sequences.

Actinomycetales is understood, in the sense used in the present invention, to mean both Actinomycetaceae such as Nocardia and Mycobacteriaceae or Rhodococcus.

There are at least 50 species of mycobacteria divided into several groups. In the present invention, the group comprising M. bovis BCG, M. bovis, M. tuberculosis, M. africanum and M. microti is referred to as the tuberculosis bacillus group; and the group comprising M. avium, M. intracellulare and M. paratuberculosis is referred to as the MAIP group.

Comparison of the nucleotide sequences of the different groups and/or species has enabled identical or similar fragments to be demonstrated within a gene common to the different groups, and a homology to be defined between the different sequences.

According to an advantageous embodiment of the invention, the said sequence possesses an at least 80% homology with the gene coding for the 65-kD mycobacterial antigen.

According to an advantageous variant of this embodiment, the said sequence comprise 383 base pairs homologous in at least 8 species of mycobacteria, namely M. tuberculosis, M. avium, M. fortuitum, M. paratuberculosis, BCG, M. kansasii, M. malmoense and M. marinum.

The 383 base pairs correspond to the expression product having an amino acid sequence of the following formula (I):

$X_1$-TYR-GLU-LYS-ILE-GLY-ALA-GLU-LEU-VAL-$X_2$-GLU-VAL-ALA-LYS-LYS-THR-ASP-ASP-VAL-ALA-$X_3$-ASP-$X_4$-THR-THR-THR-ALA-THR-VAL-LEU-$X_5$-GLN-$X_6$-LEU-VAL-$X_7$-GLU-GLY-LEU-ARG-ASN-VAL-

ALA-ALA-GLY-ALA-ASN-$X_8$-LEU-$X_9$-$X_{10}$-LYS-$X_{11}$-GLY-ILE-GLU-LYS-ALA-VAL-GLU-$X_{12}$-VAL-THR-$X_{13}$-$X_{14}$-LEU-LEU-$X_{15}$-$X_{16}$-ALA-

LYS-GLU-VAL-GLU-THR-LYS-$X_{17}$-GLN-ILE-ALA-ALA-THR-ALA-$X_{18}$-ILE-SER-$X_{19}$-GLY-ASP-$X_{20}$-SER-ILE-GLY-$X_{21}$-$X_{22}$-ILE-$X_{23}$-$X_{24}$-$X_{25}$-MET-ASP-LYS-VAL-GLY-$X_{26}$-GLU-GLY-VAL-ILE-THR-$X_{27}$-$X_{28}$-GLU-SER-$X_{29}$ in which:

$X_1$ is non-existent or represents the sequence ASP-PRO, $X_2$ represents LYS or GLU, $X_3$ represents GLY or ALA, $X_4$ represents GLY or ARG, $X_5$ represents ALA or VAL, $X_6$ represents ALA or ARG, $X_7$ represents ARG or LYS, $X_8$ represents PRO or LEU, $X_9$ represents GLY or SER, $X_{10}$ represents LEU or PHE, $X_{11}$ represents ARG or CYS, $X_{12}$ represents LYS or ALA, $X_{13}$ represents GLU or ALA, $X_{14}$ represents THR or LYS, $X_{15}$ represents LYS or ASP, $X_{16}$ represents SER, GLY, PRO or THR $X_{17}$ represents ASP or GLU, $X_{18}$ represents ALA, GLY or VAL, $X_{19}$ represents ALA or VAL, $X_{20}$ represents GLN or ALA, $X_{21}$ represents ASP or GLU, $X_{22}$ represents LEU or PRO, $X_{23}$ represents ALA or VAL, $X_{24}$ represents GLU or ASP, $X_{25}$ represents ALA or GLY, $X_{26}$ represents ASN or LYS, $X_{27}$ represents VAL or SER, $X_{28}$ represents GLU or GLY, $X_{29}$ is non-existent or represents the sequence ASN-THR-PHE-GLY-LEU-GLN.

According to another advantageous variant of this embodiment, the said sequence comprises 343 base pairs and corresponds to the formula (II) below:

```
        11         21         31         41         51         61     (II)
GTACGAGAAGA TCGGCGCTGA GCTCGTCAAG GAAGTCGCCA AGAAGACCGA CGACGTCGCG
 ATGCTCTTCT AGCCGCGACT CGAGCAGTTC CTTCAGCGGT TCTTCTGGCT GCTGCAGCGC 71         81         91        101        111        121
 GGCGACGGCA CCACCACCGC CACCGTTCTG GCACAGGCCC TGGTTCGTGA AGGTCTGCGC
 CCGCTGCCGT GGTGGTGGCG GTGGCAAGAC CGTGTCCGGG ACCAAGCACT TCCAGACGCG 131        141        151        161        171        172
 AACGTCGCTG CCGGCGCCAA CCCGCTCGGC CTGAAGCGCC GCATCGAGAA GGCCGTCGAG
 TTGCAGCGAC GGCCGCGGTT GGGCGAGCCG GACTTCGCGC CGTAGCTCTT CCCGCAGCTC 191        201        211        221        231        241
 AAGGTCACCG AGACGCTGCT GAAGAGCGCT AAGGAGGTGG AGACCAAGGA GCAGATCGCT
 TTCCAGTGGC TCTGCGACGA CTTCTCGCGG TTCCTCCACC TCTGGTTCCT CGTCTAGCGA 251        261        271        281        291        301
 GCCACCGCCG GTATCTCCGC CGGTGACCAG TGCATCGGTG ACCTGATCGC CGAGGCCATG
 CGGTGGCGGC CATAGAGGCG GCCACTGGTC AGGTAGCCAC TGGACTAGCG GCTCCGGTAC 311        321        331        341
 GACAAGGTCG GCAACGAGGG TGTCATCACC GTCGAGGAGA GC
 CTGTTCCAGC CGTTGCTCCC ACAGTAGTGG CAGCTCCTCT CG
``` and corresponds to a fragment of *M. fortuitum*, similar to the sequence of the mycobacterial gene coding for the 65-kD antigen.

The said fragment comprises, in particular, the following restriction sites:

AccII, AhaII, BanI, BanII, BbvI, Bsp1286, BstXI, CfoI, DdeI, EcoRII, EspI, Fnu4HI, HaeII, HaeIII, HapII, HgaI, HinfI, HphI, MaeIII, MboII, MnlI, NarI, NcoI, NlaIII, SacI, SacII, Sau3A, Sau96A, ScrFI, StyI, TaqI, YmaIII.

According to another advantageous variant of this embodiment, the said sequence comprises 343 base pairs and corresponds to the formula (III) below:

```
1       11         21         31         41         51         61     (III)
GTACGAGAAGA TCGGCGCCGA GCTGGTCAAG GAAGTCGCCA AGAAGACCGA CGACGTCGCC
 ATGCTCTTCT AGCCGCGGCT CGACCAGTTC CTTCAGCGGT TCTTCTGGCT GCTGCAGCGG
```

```
        71          81           91         101         111         121
GGTGACGGCA  CGACGACGGC  CACGGTGCTC  GCCCAGGCGT  TGGTCCGCGA  GGGCGTGCGC
CCACTGCCGT  GCTGCTGCCG  GTGCCACGAG  CGGGTCCGCA  ACCAGGCGCT  CCCGGACGCG 131         141         151         161         171         181
AACGTCGCGG  CCGGCGCCAA  CCTGCTCTGT  CTCAAGCGCG  GCATCGAGAA  GGCCGTCGAG
TTGCAGCGCC  GGCCGCGGTT  GGGCGACCCA  GAGTTCGCGC  CGTAGCTCTT  CCGGCAGCTC 191         201         211         221         231         241
AAGGTCACCG  AGACCCTGCT  CAAGTCGGCC  AAGGAGGTCG  AGACCAAGGA  CCAGATCGCT
TTCCAGTGGC  TCTGGGACGA  GTTCAGCCGG  TTCCTCCAGC  TCTGGTTCCT  GGTCTAGCGA 251         261         271         281         291         301
GCCACCGCGG  CCATCTCCGC  GGGCGACCAG  TCGATCGGCG  ACCTGATCGC  CGAGGCGATG
CGGTGGCGCC  GGTAGAGGCG  CCCGCTGGTC  AGCTAGCCGC  TGGACTAGCG  GCTCCGCTAC 311         321         331         341
GACAAGGTCG  GCAACGAGGG  CGTCATCACC  GTCGAGGAGT  CC
CTGTTCCAGC  CGTTGCTCCC  GCAGTAGTGG  CAGCTCCTCA  GG
``` and corresponds to a fragment common to the MAIP group similar to the sequence of the mycobacterial gene coding for the 65-kD antigen.

The said fragment comprises, in particular, the following restriction sites:

AccII, AfII, AhaII, BanI, BbvI, BgII, Bsp1286, BstEII, BstXI, CfoI, EaeI, HaeII, HaeIII, HphI, MaeIII, MnII, NarI, PvuI, SacII, Sau3A, Sau96A, TaqI.

According to another advantageous variant of this embodiment, the said sequence comprises 343 nucleotides and corresponds to the formula (IV) below:

The said fragment comprises, in particular, the following restriction sites:

AccII, AhaII, BanI, BbvI, BstXI, CfoI, EaeI, HaeIII, HphI, MaeIII, MnII, NarI, NrvI, SacII, Sau3A, Sau96A, TaqI.

According to yet another advantageous variant of this embodiment, the said sequence comprises 343 nucleotides and corresponds to the formula (V) below:

```
1         11          21          31          41          51          61                  (IV)
GTACGAGAAGA TCGGCGCCGA GCTGGTCAAA GAGGTAGCCA AGAAGACCGA TGACGTCGCC
ATGCTCTTCT  AGCCGCGGCT  CGACCAGTTT  CTCCATCGGT  TCTTCTGGCT  ACTGCAGCGG 71          81          91         101         111         121
GGTGACGGCA  CCACGACGGC  CACCGTGCTG  GCCCAGGCGT  TGGTTCGCGA  GGGCCTGCGC
CCACTGCCGT  GGTGCTGCCG  GTGGCACGAC  CGGGTCCGCA  ACCAAGCGCT  CCCGGACGCG 131         141         151         161         171         181
AACGTCGCGG  CCGGCGCCAA  CCCGCTCGGT  CTCAAACGCG  GCATCGAAAA  GGCCGTGGAG
TTGCAGCGCC  GGCCGCGGTT  GGGCGAGCCA  GAGTTTGCGC  CGTAGCTTTT  CCGGCACCTC 191         201         211         221         231         241
AAGGTCACCG  AGACCCTGCT  CAAGGGCGCC  AAGGAGGTCG  AGACCAAGGA  GCAGATTGCG
TTCCAGTGGC  TCTGGGACGA  GTTCCCGCGG  TTCCTCCAGC  TCTGGTTCCT  CGTCTAACGC 251         261         271         281         291         301
GCCACCGCAG  CGATTTCGGC  GGGTGACCAG  TCCATCGGTG  ACCTGATCGC  CGAGGCGATG
CGGTGGCGTC  GCTAAAGCCG  CCCACTGGTC  AGGTAGCCAC  TGGACTAGCG  GCTCCCCTAC 311         321         331         341
GACAAGGTGG  GCAACGAGGG  CGTCATCACC  GTCGAGGAGT  CC
CTGTTCCACC  CGTTGCTCCC  GCAGTAGTGG  CAGCTCCTCA  GG
``` and corresponds to a fragment of the sequence of the gene coding for the 65-kD antigen of the tuberculosis bacillus group.

```
            10          20          30          40          50          60
         GTACGAGAAG ATCGGCGCCG AGCTGGTCGA GGAAGTCGCC AAGAAGACCG ACGACGTCGC
         CATGCTCTTC TAGCCGCGGC TCGACCAGCT CCTTCAGCGG TTCTTCTGGC TGCTGCAGCG
```

```
              70         80         90        100        110        120
         CGGCGACGGC ACCACCACGG CCACTGTGCT CGCGCAGGCG TTGGTCAAAG AGGGCCTGCG
         GCCGCTGCCG TGGTGGTGCC GGTGACACGA GCGCGTCCGC AACCAGTTTC TCCCGGACGC 130        140        150        160        170        180
         CAACGTCGCG GCCGGCGCCA ACCCACTGGG CCTGAAGCGC GGCATCGAGA AGGCAGTCGA
         GTTGCAGCGC CGGCCGCGGT TGGGTGACCC GGACTTCGCG CCGTAGCTCT TCCGTCAGCT 190        200        210        220        230        240
         GAAGGTCACC GAGACGCTGC TCAAGGGCGC CAAGGAGGTG GAGACCAAGG AGCAGATCGC
         CTTCCAGTGG CTCTGCGACG AGTTCCCGCG GTTCCTCCAG CTCTGGTTCC TCGTCTAGCG 250        260        270        280        290        300
         TGCCACCGCG GCCATCTCCG CCGGTGACCA GTCGATCGGC GACCTGATCG CCGATGGCAT
         ACGGTGGCGC CGGTAGAGGC GGCCACTGGT CAGCTAGCCG CTGGACTAGC GGCTACCGTA 310        320        330        340       343
         GGACAAGGTC GGCAACGAGG GTGTCATCAC CGTTGAGGAG TCC
         CCTGTTCCAG CCGTTGCTCC CACAGTAGTG GCAACTCCTC AGG
``` and corresponds to a fragment of *Mycobacterium kansasii* similar to the sequence of the mycobacterial gene coding for the 65-kD antigen.

The said fragment comprises, in particular, the following restriction sites:

AccII, AhaII, AluI, AosI, BanI, BglI, Bsp1286, BstEII, CfoI, EaeI, HapII, HgaI, HphI, MboII, MnlI, NaeI, NlaIII, RsaI, Sau3A, Sau96A, SfaNI, StyI, TaqI, TthIIII.

According to another advantageous variant of this embodiment, the said sequence comprises 343 nucleotides and corresponds to the formula (VI) below:

```
              10         20         30         40         50         60
         CTACGAGAAG ATCGGCGCCG AGCTGGTCAA GGAAGTCGCC AAGAAGACCG ACGACGTGGG
         GATGCTCTTC TAGCCGCGGC TCGACCAGTT CCTTCAGCGG TTCTTCTGGC TGCTGCACCC 70         80         90        100        110        120
         CGGTGACCGG ACGACGACGG CCACCGTGCT GGTGCAGGCG CTGGTCAAAG AGGGCCTGCG
         GCCACTGGCC TGCTGCTGCC GGTGGCACGA CCACGTCCGC GACCAGTTTC TCCCGGACGC 130        140        150        160        170        180
         CAACGTCGCG GCCGGTGCCA ACCTGCTCAG CTTCAAGTGC GGCATCGAGA AGGCGGTCGA
         GTTGCAGCGC CGGCCACGGT TGGACGAGTC GAAGTTCACG CCGTAGCTCT TCCGCCAGCT 190        200        210        220        230        240
         GAAGGTCACC GAGACCCTGC TCAAGCCGGC CAAGGAGGTC GAGACCAAGG AGCAGATCGC
```

```
                                       -continued
CTTCCAGTGG CTCTGGGACG AGTTCGGCCG GTTCCTCCAG CTCTGGTTCC TCGTCTAGCG

.........  .........  .........  .........  .........  .........

250        260        270        280        290        300
CGCCACCGCC GTCATCTCGG TGGGCGACCA GTCGATCGGT GACCTGATCG CCGAGGCGAT
GCGCTGGCGG CACTAGAGCC ACCCGCTGGT CAGCTAGCCA CTGGACTAGC GGCTCCGCTA

.........  .........  .........  .........  .........  .........

310        320        330        340    343
GGACAAGGTT GGCAACGAGG GCGTCATCAC CGTCGAGGAG TCC
CCTGTTCCAA CCGTTGCTCC CGCAGTAGTG GCAGCTCCTC AGG
``` and corresponds to a fragment of *Mycobacterium malmoense* similar to the sequence of the mycobacterial gene coding for the 65-kD antigen.

The said fragment comprises, in particular, the following restriction sites:

AccII, AhaII, AluI, AosI, BanI, BstEII, EaeI, EspI, Fnu4HI, HaeII, HinfI, HphI, MboII, MnlI, NaeI, Sau3A, StyI, TaqI.

According to yet another advantageous variant of this embodiment, the said sequence comprises 343 nucleotides and corresponds to the formula (VII) below:

and corresponds to a fragment of *Mycobacterium marinum*, similar to the sequence of the mycobacterial gene coding for the 65-kD antigen.

The said fragment comprises, in particular, the following restriction sites:

AatI, AosI, AhaII, AluI, BbvI, BstEII, CfoI, EaeI, Fnu4HI, HaeII, HapII, HinfI, MboII, MnlI, NaeI, PvuI, Sau3A, StyI, TaqI, TthIIII.

According to another advantageous variant of this embodiment, the said sequence comprises 343 nucleotides and corresponds to the formula (VIII) below:

```
        10         20         30         40         50         60
CTACGAGAAG ATCGGCGCCG AGCTGGTCAA AGAGGTCGCC AAGAAGACCG ACGATGTCGC
GATGCTCTTC TAGCCGCGGC TCGACCAGTT TCTCCAGCGG TTCTTCTGGC TGCTACAGCG

.........  .........  .........  .........  .........  .........

70         80         90        100        110        120
CGGTGACCGG ACCACCACGG CCACCGTGCT GGCACAGGCG CTGGTCAAGG AAGGCCTGCG
GCCACTGGCC TGGTGGTGCC GGTGGCACGA CCGTGTCCGC GACCAGTTCC TTCCGGACGC

.........  .........  .........  .........  .........  .........

130        140        150        160        170        180
CAACGTTGCG GCCGGTGCCA ACCCGCTCGG TCTGAAGCGC GGCATTGAGA AGGCAGTCGA
GTTGCAACGC CGGCCACGGT TGGGCGAGCC AGACTTCGCG CCGTAACTCT TCCGTCAGCT

.........  .........  .........  .........  .........  .........

190        200        210        220        230        240
GAAGGTCACC GAGACCTTGC TCAAGTCGGC CAAAGAGGTC GAGACCAAGG AGCAGATCGC
CTTCCAGTGG CTCTGGAACG AGTTCAGCCG GTTTCTCCAG CTCTGGTTCC TCGTCTAGCG

.........  .........  .........  .........  .........  .........

250        260        270        280        290        300
GGCGACCGCA GCCATCTCCG CCGGCGACCA GTCGATCGGC GACCCGATCG TCGAGGCGAT
CCGCTGGCGT CGCTAGAGGC GGCCGCTGGT CAGCTAGCCG CTGGGCTAGC AGCTCCGCTA

.........  .........  .........  .........  .........  .........

310        320        330        340    343
GGACAAGGTC GGCAACGAGG GCGTCATTAC CGTCGAGGAG TCC
CCTGTTCCAG CCGTTGCTCC CGCAGTAATG GCAGCTCCTC AGG

.........  .........  .........  .........  .........  .........
```

```
           10         20         30         40         50         60
    CTACGAGAAG ATCGGCGCCG AGCTGGTCAA GGAAGTCGCC AAGAAGACCG ACGACGTCGC
    GATGCTCTTC TAGCCGCGGC TCGACCAGTT CCTTCAGCGG TTCTTCTGGC TGCTGCAGCG 70         80         90        100        110        120
    GGCTGACGGC ACCACCACCG CCACCGTGCT CGCCCAGCGG CTGGTGCGCG AGGGTCTGCG
    CCGACTGCCG TGGTGGTGGC GGTGGCACGA GCGGGTCGCC GACCACGCGC TCCCAGACGC 130        140        150        160        170        180
    CAACGTGGCC GCGGGCGCGA ACCCGCTGGG CCTCAAGCGC GGCATCGAGA AGGCCGTCGA
    GTTGCACCGG CGCCCGCGCT TGGGCGACCC GGAGTTCGCG CCGTAGCTCT TCCGGCAGCT 190        200        210        220        230        240
    GGCCGTGACC GCCAAGCTGC TCGACACCGC CAAGGAGGTC GAGACCAAGG AGCAGATCGC
    CCGGCACTGG CGGTTCGACG AGCTGTGGCG GTTCCTCCAG CTCTGGTTCC TCGTCTAGCG 250        260        270        280        290        300
    CGCCACCGCG GGCATCTCCG CGGGCGACGC GTCCATCGGT GAGCTGATCG CCGAGGCCAT
    GCGGTGGCGC CCGTAGAGGC GCCCGCTGCG CAGGTAGCCA CTCGACTAGC GGCTCCGGTA 310        320        330        340        343
    GGACAAGGTC GGCAAGGAAG GCGTCATCAC CGTCGAGGAG AGC
    CCTGTTCCAG CCGTTCCTTC CGCAGTAGTG GCAGCTCCTC TCG
``` and corresponds to a fragment of *Nocardia asteroides*, similar to the sequence of the mycobacterial gene coding for the 65-kD antigen.

The said fragment comprises, in particular, the following restriction sites:

AccII, AhaII, AluI, AosI, BanI, Bsp1286, CfoI, EaeI, Fnu4HI, HaeIII, HgaI, HphI, MaeIII, MboII, MnlI, NlaIII, SacII, Sau3A, Sau96A, SfaNI, StyI, TaqI, TthIIII.

The subject of the present invention is also oligonucleotides, characterised in that they consist of a fragment of a nucleotide sequence according to the invention.

Among these fragments, special mention may be made of the following:

an oligonucleotide characterised in that it possesses the following sequence of formula (IX):

$$\text{5' GAGATCGAGCTGGAGGATCC} \tag{IX}$$

Such a sequence corresponds, in particular, to the base sequence 397–416 after the start codon of the "+" strand of the gene coding for the 65-kd antigen of the tuberculosis bacillus group; this sequence is hereinafter designated TB-1;

an oligonucleotide, characterised in that it possesses the following sequence of formula (X):

$$\text{5' AGCTGCAGCCCAAAGGTGTT} \tag{X}$$

Such a sequence is complementary to the base sequence 535–554 after the start codon of then "+" strand of the gene coding for the 65-kD antigen of the tuberculosis bacillus group; this sequence is hereinafter designated TB-2;

an oligonucleotide, characterised in that it possesses the following sequence of formula (XI):

$$\text{5' GCGGCATCGAAAAGGCCGTG} \tag{XI}$$

which sequence permits recognition of tuberculosis bacilli and is hereinafter designated TB-3;

an oligonucleotide, characterised in that it possesses the following sequence of formula (XII):

$$\text{5' CGAAATCGCTGCGGTGGCCG} \tag{XII}$$

which sequence permits recognition of tuberculosis bacilli and is hereinafter designated TB-4;

an oligonucleotide, characterised in that it possesses the following sequence of formula (XIII):

$$\text{5' CTGCCACCGCGGCCATCTCC} \tag{XIII}$$

which sequence permits recognition of MAIP group bacilli and is hereinafter designated TB-5; this oligonucleotide advantageously comprises a single BglI restriction site;

an oligonucleotide, characterised in that it possesses the following sequence of formula (XIV):

$$\text{5' CTGCCACCGCCGGTATCTCC} \tag{XIV}$$

which sequence permits recognition of *M. fortuitum* and is hereinafter designated TB-6;

an oligonucleotide, characterised in that it possesses the following sequence of formula (XV):

5' AACGTCGCGGCCGGCGCCAA 3' (XV)

which sequence is hereinafter designated TB-7;

an oligonucleotide, characterised in that it possesses the following sequence of formula (XVI);

5' GACTCCTCGACGGTGATGAC 3' (XVI)

which sequence is hereinafter designated TB-8;

an oligonucleotide, characterised in that it possesses the following sequence of formula (XVII):

5' CCTGCTCAAGGGCGCCAAG 3' (XVII)

which sequence is hereinafter designated TB-9; this oligonucleotide TB-9 advantageously comprises a single BanI restriction site.

an oligonucleotide, characterised in that it possesses the following sequence of formula (XVIII):

3' CGAAATCGCTGCGGTGGCCGCAATCTGCTC 5' (XVIII)

which sequence permits recognition of tuberculosis group bacilli and is hereinafter designated TB-10.

an oligonucleotide, characterised in that it possesses the following sequence of formula (XIX):

5' GGTGCTCGCCCAGGCGTTGGTCCGC 3' (XIX)

which sequence permits recognition of MAIP group bacilli and is hereinafter designated TB-11.

an oligonucleotide, characterised in that it possesses the following sequence of formula (XX):

5' TGTGCTCGCGCAGGCGCTGGTCAAA 3' (XX)

which sequence permits specific recognition of *M. kansasii* and is hereinafter designated TE-12.

According to yet another embodiment, the said oligonucleotides are obtained synthetically using, in particular, an apparatus marketed by APPLIED BIOSYSTEMS (U.S.A.).

The subject of the present invention is also pairs of primers for the synthesis of an Actinomycetales DNA or RNA, characterised in that each primer comprises a nucleotide sequence or a fragment of a nucleotide sequence as defined above.

Such primers permit the synthesis of a DNA or RNA sequence or a fragment of the latter present in a gene coding for an antigen present in all Actinomycetales, and in particular the gene coding for the 65-kD antigen.

According to an embodiment of the said pairs of primers, they advantageously consist of an oligonucleotide of formula (IX) (TB-1) paired with an oligonucleotide of formula (X) (TB-2).

According to another embodiment of the said pairs of primers, they advantageously consist of an oligonucleotide of the formula (XV) (TB-7) paired with an oligonucleotide of formula (XVI) (TB-8).

The primers TB-1 and TB-2 permit the synthesis of a DNA or RNA sequence present in mycobacteria or related bacteria such as *Nocardia* or *Rhodococcus*.

The subject of the present invention is also nucleotide probes, characterised in that they comprise a nucleotide sequence or a fragment of the latter as defined above, where appropriate labelled using a label such as a radioactive isotope, a suitable enzyme, a fluorochrome, an antibody or a base analogue such as that described in French Patent No. 81/24,131.

According to an advantageous embodiment of this invention, the said probe is chosen from the group comprising the oligonucleotides of formulae XI (TB-3), XII (TB-4), XIII (TB-5), XIV (TB-6), XVII (TB-9), XVIII (TB-10), XIX (TB-11) and XX (TB-12).

The probe TB-6 enables *M. fortuitum* to be detected in particular; the probes TB-5 and TB-11 enable MAIP group mycobacteria to be detected; the probes TB-3, TB-4, TB-9 and TB-10 enable mycobacteria of the tuberculosis bacillus group to be detected; and the probe TB-12 enables *M. kansasii* to be detected.

The subject of the present invention is also the peptides or peptide fragments encoded by any one of the sequences defined above. The following may be mentioned in particular:

a peptide and/or peptide fragment, characterised in that it is encoded by the sequence of 343 nucleotides of formula (II) above and corresponds to the formula (XXI) below:

TYR-GLU-LYS-ILE-GLY-ALA-GLU-LEU-VAL-LYS-GLU-VAL-ALA-LYS-LYS-THR-ASP-ASP-VAL-ALA-GLY-ASP-GLY-THR-THR-THR-ALA-THR-VAL-LEU-ALA-GLN-ALA-LEU

-VAL-ARG-GLU-GLY-LEU-ARG-ASN-VAL-ALA-ALA-GLY-ALA-ASN-PRO-LEU-GLY-LEU-LYS-ARG-GLY-ILE-GLU-LYS-ALA-VAL-GLU-LYS-VAL-THR-GLU-THR-LEU-LEU-LYS-SERALA-LYS-ALA-VAL-GLU-THR-LYS-GLU-GLN-ILE-ALA-ALA-THR-ALA-GLY-ILE-SER-ALA-GLY-ASP-GLN-SER-ILE-GLY-ASP-LEU-ILE-ALA-GLU-ALA-MET-ASP-LYS-VAL-GLY-ASN-GLU-GLY-VAL-ILE-THR-VAL-GLU-GLU-SER. (XXI)

a peptide and/or peptide fragment, characterised in that it is encoded by the sequence of 343 nucleotides of formula (III) above and corresponds to the formula (XXII) below:

TYR-GLU-LYS-ILE-GLY-ALA-GLU-LEU-VAL-LYS-GLU-VAL-ALA-LYS-LYS-THR-ASP-ASP-VAL-ALA-GLY-ASP-GLY-THR-THR-THR-ALA-THR-VAL-LEU-ALA-GLN-ALA-LEU-VAL-ARG-GLU-GLY-LEU-ARG-ASN-VAL-ALA-ALA-GLY-ALA-ASN-PRO-LEU-GLY-LEU-LYS-ARG-GLY-ILE-GLU-LYS-ALA-VAL-GLU-LYS-VAL-THR-GLU-THR-LEU-LEU-LYS-SER

-ALA-LYS-GLU-VAL-GLU-THR-LYS-ASP-GLN-ILE-ALA-ALA-THR-ALA-ALA-ILE-SER-ALA-GLY-ASP-GLN-SER-ILE-GLY-ASP-LEU-ILE-ALA-GLU-ALA-MET-ASP-LYS-VAL-GLY-ASN-GLU-GLY-VAL-ILE-THR-VAL-GLU-GLU-SER. (XXII)

a peptide and/or peptide fragment, characterised in that it is encoded by the sequence of 343 nucleotides of formula (V) and corresponds to the formula (XXIII) below:

TYR-GLU-LYS-ILE-GLY-ALA-GLU-LEU-VAL-GLU-GLU-VAL-ALA-LYS-LYS-THR-ASP-ASP-VAL-ALA-GLY-ASP-GLY-THR-THR-THR-ALA-THR-VAL-LEU-ALA-GLN-ALA-LEU-VAL-LYS-GLU-GLY-LEU-ARG-ASN-VAL-ALA-ALA-GLY-ALA-ASN-PRO-LEU-GLY-LEU-LYS-ARG-GLY-ILE-GLU-LYS-ALA-VAL-GLU-LYS-VAL-THR-GLU-THR-LEU-LEU-LYS-GLY

-ALA-LYS-GLU-VAL-GLU-THR-LYS-GLU-GLN-ILE-ALA-ALA-THR-ALA-ALA-ILE-SER-ALA-GLY-ASP-GLN-SER-ILE-GLY-ASP-LEU-ILE-ALA-ASP-GLY-MET-ASP-LYS-VAL-GLY-ASN-GLU-GLY-VAL-ILE-THR-SER-GLY-GLU-SER (XXIII)

a peptide and/or peptide fragment, characterised in that it is encoded by the sequence of 343 nucleotides of formula (VI) and corresponds to the formula (XXIV) below:

TYR-GLU-LYS-ILE-GLY-ALA-GLU-LEU-VAL-LYS-GLU-VAL-
ALA-LYS-LYS-THR-ASP-ASP-VAL-ALA-GLY-ASP-ARG-
THR-THR-THR-ALA-THR-VAL-LEU-VAL-GLN-ALA-LEU-
VAL-LYS-GLU-GLY-LEU-ARG-ASN-VAL-ALA-ALA-GLY-
ALA-ASN-LEU-LEU-SER-PHE-LYS-CYS-GLY-ILE-GLU-
LYS-ALA-VAL-GLU-LYS-VAL-THR-GLU-THR-LEU-LEU-
LYS-PRO

-ALA-LYS-GLU-VAL-GLU-THR-LYS-GLU-GLN-ILE-ALA-
ALA-THR-ALA-VAL-ILE-SER-VAL-GLY-ASP-GLN-SER-
ILE-GLY-ASP-LEU-ILE-ALA-GLU-ALA-MET-ASP-LYS-
VAL-GLY-ASN-GLU-GLY-VAL-ILE-THR-VAL-GLU-GLU-
SER.                                                         (XXIV)

a peptide and/or peptide fragment, characterised in that it is encoded by the sequence of 343 nucleotides of formula (VII) and corresponds to the formula (XXV) below:

ASP-PRO-TYR-GLU-LYS-ILE-GLY-ALA-GLU-LEU-VAL-LYS-
GLU-VAL-ALA-LYS-LYS-THR-ASP-ASP-VAL-ALA-GLY-
ASP-ARG-THR-THR-THR-ALA-THR-VAL-LEU-ALA-GLN-
ALA-LEU-VAL-LYS-GLU-GLY-LEU-ARG-ASN-VAL-ALA-
ALA-GLY-ALA-ASN-PRO-LEU-GLY-LEU-LYS-ARG-GLY-
ILE-GLU-LYS-ALA-VAL-GLU-LYS-VAL-THR-GLU-THR-
LEU-LEU

-LYS-SER-ALA-LYS-GLU-VAL-GLU-THR-LYS-GLU-GLN-ILE-
ALA-ALA-THR-ALA-ALA-ILE-SER-ALA-GLY-ASP-GLN-
SER-ILE-GLY-ASP-PRO-ILE-VAL-GLU-ALA-MET-ASP-
LYS-VAL-GLY-ASN-GLU-GLY-VAL-ILE-THR-VAL-GLU-
GLU-SER-ASN-THR-PHE-GLY-LEU-GLN.        (XXV)

a peptide and/or peptide fragment, characterised in that it is encoded by the sequence of 343 nucleotides of formula (VIII) and corresponds to the formula (XXVI) below:

TYR-GLU-LYS-ILE-GLY-ALA-GLU-LEU-VAL-LYS-GLU-VAL-
ALA-LYS-LYS-THR-ASP-ASP-VAL-ALA-ALA-ASP-GLY-
THR-THR-THR-ALA-THR-VAL-LEU-ALA-GLN-ALA-LEU-
VAL-ARG-GLU-GLY-LEU-ARG-ASN-VAL-ALA-ALA-GLY-
ALA-ASN-PRO-LEU-GLY-LEU-LYS-ARG-GLY-ILE-GLU-
LYS-ALA-VAL-GLU-ALA-VAL-THR-ALA-LYS-LEU-LEU-
ASP-THR

-ALA-LYS-GLU-VAL-GLU-THR-LYS-GLU-GLN-ILE-ALA-
ALA-THR-ALA-GLY-ILE-SER-ALA-GLY-ASP-ALA-SER-
ILE-GLY-GLU-LEU-ILE-ALA-GLU-ALA-MET-ASP-LYS-
VAL-GLY-LYS-GLU-GLY-VAL-ILE-THR-VAL-GLU-GLU-
SER.                                                         (XXVI)

The subject of the present invention is also a composition having immunogenic capability, characterised in that it comprises at least one peptide and/or peptide fragment as defined above, optionally combined with at least one pharmaceutically acceptable vehicle.

The subject of the present invention is also polyclonal or monoclonal antibodies, characterised in that they are obtained by immunisation of a suitable animal with a peptide or peptide fragment according to the invention.

Such antibodies can, in particular, find application for demonstrating the presence of mycobacteria in a suitable sample obtained from a patient to be tested, according to a known method of the ELISA or RIA type.

The subject of the present invention is also a method for the detection and rapid identification, by amplification and hybridisation, of small amounts of Actinomycetales chosen from the group comprising mycobacteria, *Nocardia* and *Rhodococcus*, possibly present in a biological sample suitably treated to extract the DNA and/or the transcription products of the said Actinomycetales, which method is characterised in that the said sample:

(1) is brought into contact with a pair of primers according to the invention, to amplify at least one fragment of the said DNA or RNA, (2) after which the amplified DNA or RNA sequence is detected by at least one nucleotide probe according to the invention.

The method carried out in (1) is, in particular, one of the techniques of genetic amplification such as the so-called Qβ replicase method (LIZARDI P. M. et al., Biotechnol., 1988, 6) or the so-called PCR (polymerase chain reaction) method described in European Patent Applications No. 200,363, No. 201,184 and No. 229,701 filed by CETUS CO.

Such a method has the advantage of enabling a specific, direct and rapid test distinguishing the different groups of Actinomycetales, and in particular of mycobacteria, to be carried out, on the one hand using non-specific primers which amplify a DNA or RNA fragment, and on the other hand using group- or genus-specific probes.

According to an advantageous embodiment of the said method, it comprises in addition:

(3) cleavage of any probe which has hybridised during the above step (2), using a suitable restriction enzyme;

(4) detection of any probe fragment obtained.

According to a variant of this embodiment, the restriction enzyme is advantageously chosen from the group comprising BanI and BglI.

Such an embodiment has the advantage of enabling a genus or a group of Actinomycetales to be detected.

According to another advantageous embodiment of the said method, the detection of the amplified DNA or RNA sequence is carried out using two suitable nucleotide probes, the said method comprising in addition:

(3) enzymatic coupling of the two hybridised probes;

(4) detection of any fragment obtained containing the two combined probes.

According to another advantageous embodiment of the said method, the DNA is isolated from the biological sample during a step prior to the detection and identification steps, by suspending the centrifugation pellet from the said biological sample in a suitable lysis solution, followed by an incubation at approximately 95° C. for a suitable time, the incubation itself being followed by the addition of a buffer solution to the medium, after which the DNA is extracted by suitable means of extraction.

According to an advantageous variant of this embodiment, the lysis solution employed is a solution comprising 0.1N NaOH, 2M NaCl and 0.5% SDS.

According to another advantageous variant of this embodiment, the incubation is carried out at a temperature of approximately 95° C. for approximately 15 minutes.

The subject of the present invention is, in addition, a ready-to-use kit, outfit or coordinated set for carrying out the method for detecting at least one Actinomycetales bacterium, in particular at least one mycobacterium, characterised in that it comprises, apart from the appropriate amounts of suitable buffers and reagents for carrying out the said detection:

suitable doses of a pair of primers according to the invention;

suitable doses of at least one nucleotide probe or probe fragment according to the invention.

Apart from the foregoing variants, the invention comprises yet other variants which will become apparent from the description which follows, which relates to examples of implementation of the method which is the subject of the present invention.

It should, however, be clearly understood that these examples are given only by way of illustration of the subject of the invention and in no way constitute a limitation of the latter.

EXAMPLE 1

Detection and comparative identification of *M. tuberculosis, M. bovis, M. avium* and *M. fortuitum*.

a) Isolation of mycobacterial DNA.

The biological extracts are treated in a suitable manner and then centrifuged. To extract the DNA, the centrifugation pellet is resuspended in 50 μl of 0.1N NaOH containing 2M NaCl and 0.5% SDS and incubated at 95° C. for 15 min (occasional gentle shaking), and then, after the addition of 0.4 ml of 0.1M Tris-HCl, pH 7, the DNA is extracted by three treatments with a phenol/chloroform mixture, precipitated with ethanol and dissolved in 50 μl of 10 mM Tris-HCl, pH 8, containing 0.1 mM EDTA.

b) DNA amplification.

Amplification is carried out as described in SAIKI et al. (Science, 1988, vol. 239, 487–491) and also in European Patent Application No. 200,362: 0.1 ml of a reaction mixture containing 50 mM KCl, 10 mM Tris-HCl (pH 8.3), 1.5–2.4 mM $MgCl_2$, 100 μg/ml of gelatin, 300 μM deoxyribonucleotides (mixture of the 4 deoxyribonucleotides dA, dG, dC and dI), 50 pM of the primers according to the invention designated TB-1 and TB-2, two units of Taq polymerase and 10–50 μl of an extract of a mixture of human cells and mycobacteria or 50 ng of DNA extracted from mycobacteria is maintained at 94° C. (1.5 min), 50° C. (2 min) and 72° C. (2 min) for approximately 40 cycles. After the last cycle, the samples are maintained at 37° C. for 10 min and then stored at 4° C.

c. Analysis of the amplified samples by Southern blot analysis.

10 μl aliquots are removed from the amplified samples and subjected to electrophoresis on 2% agarose gel. The DNA is then transferred onto nylon filters (standard technique: REED K. L. et al., Nucleic Acid Research, 1985, 13, 7207). The filters with DNA are then washed in 2× SSPE solution (20× SSPE solution corresponds to 3.0M NaCl, 200 mM $NaH_2PO_4$ and 20 mM EDTA), then treated with a prehybridisation mixture at 63° C. in a solution comprising 5× SSPE and 5× Denhardt (1× Denhardt solution corresponds to 0.02% of Ficoll, 0.02% of polyvinylpyrrolidone and 0.02% of bovine serum albumin) for 2 hours and then hybridised in the same solution containing three probes according to the invention, TB-4, TB-5 and TB-6, labelled at their 5' end with $^{32}P$ ($2 \times 10^5$ cpm/ml, specific activity 1–3 μCi/pmol) overnight at 63° C. The blots or deposits obtained are washed for 2 hours at room temperature in 0.1× SSC solution (1× SSC corresponds to 0.15M NaCl and 0.015M Na citrate) containing 0.5% SDS for 2 to 4 minutes at 67°–72° C. in 5× SSPE solution containing 0.5% SDS and 2 hours at room temperature in 0.1× SSC containing 0.5% SDS. The deposits obtained are dried and any hybrids present are visualised by exposure to an XAR-5 film.

In dot-blot analysis, 10 μl of aliquots of amplified samples are denatured by heating to 95° C. for 2 min in 0.2 ml of 0.4M NaOH containing 25 mM EDTA. The samples are cooled rapidly and loaded into the wells of a manifold (BIORAD, (U.S.A.)) or minifold (CERA LABO (France)) fitted with a nylon membrane. Each well is washed twice with 0.4 ml of 20× SSPE, the membrane is heated to 80° C. for one hour and hybridisation is carried out as described above. The results as seen in FIG. 1 are obtained.

FIG. 1 shows the hybridisation of amplified DNA of *M. bovis* (B), *M. avium* (A) and *M. fortuitum* (F) with the specific probes TB-4, TB-5 and TB-6, respectively.

EXAMPLE 2

Comparison of sequences obtained in Example 1 with the DNA sequences as described in the literature.

a) Sequencing of the amplified mycobacterial sequences obtained.

The DNA is extracted with phenol, precipitated with ethanol and redissolved in 10 mM Tris-HCl (pH 8) containing 1 mM EDTA.

The DNA is then digested with the restriction endonucleases PstI and BamHI, cloned into the phages M13mp18 and M13mp19 and sequenced according to SANGER's method using T7 polymerase or Taq polymerase in the presence of d-azaGTP in place of dGTP.

The amplified DNA corresponds to the expected region of the gene coding for the 65-kD mycobacterial antigen, as shown in FIG. 2, in which the DNA sequences of the amplified fragments obtained from the gene coding for the 65-kD antigen of *M. bovis, M. avium, M. paratuberculosis* and *M. fortuitum* are specified.

The sequence of the amplified DNA of *M. bovis* is identical to the corresponding region of the sequence coding for the 65-kD antigen of *M. bovis* (THOLE et al. 1987) and *M. tuberculosis* (SHINNICK et al. 1987).

The sequences of the amplified DNA from *M. avium, M. paratuberculosis* and *M. fortuitum* are very similar to those of *M. bovis* and *M. tuberculosis*, and the deduced translation products corresponding to these sequences are also very similar to the 65-kD antigen of *M. bovis/M. tuberculosis* as shown in FIG. 2.

FIG. 3 shows a number of restriction sites of the fragments of 343 nucleotides contained within the gene coding for the 65-kD antigen of *M. avium* (FIG. 3a), *M. fortuitum* (FIG. 3b), *M. paratuberculosis* (FIG. 3c) and *M. bovis* BCG (FIG. 3d).

EXAMPLE 3

Development of the sensitivity of the method.

The sensitivity of the method was tested using BCG diluted in a biological medium, pleural fluid. It was possible to detect approximately 10 bacilli per ml of fluid; this represents a considerable improvement on the direct examination tests, which require $10^3$ to $10^4$ bacilli/ml for the detection of mycobacteria, and without identification.

Furthermore, this test may be accomplished much more rapidly than the detection and identification of mycobacteria after enrichment and culturing.

FIG. 4 shows the results obtained for the DNA extracted from samples containing $10^6$ human mononuclear blood cells and $6 \times 10^5$ (column 1), $6 \times 10^4$ (column 2), $6 \times 10^3$ (column 3), 600 (column 4), 60 (column 5) and 6 (column 6) *M. bovis* bacilli, and amplified using Taq polymerase and the oligonucleotide primers TB-1 and TB-2 (FIG. 4a: gel; FIG. 4b: dot blot)

EXAMPLE 4

Detection of amplified sequences of the tuberculosis bacillus group by the aligonucleotide restriction test.

To detect the presence of amplified sequences of mycobacteria belonging to the tuberculosis bacillus group by the restriction test, $4 \times 10^4$ cpm of oligonucleotide TB-9 labelled with $^{32}P$ at its 5' end is mixed with 2 μl of a 10× buffer (40 mM Tris-HCl pH 7.0, 60 mM $MgCl_2$ and 60 mM 2-mercaptoethanol) in a final volume of 15 μl. 4 μl of amplified product are added and the tube is incubated at 95° C. for 5 minutes, transferred to ice and then incubated at 52° C. for 2 hours. 1 μl of BanI (25 units) is added and the tubes are incubated at 37° C. for 1–2 hours. 4 μl of 95% formamide containing 20% of Ficoll, 25 mM EDTA, 25 μg/ml of bromophenol blue and 25 μg/ml of xylene cyanol are added, the tubes are heated to 65° C. for 10 minutes and 12 μl are subjected to electrophoresis on a 30% polyacrylamide gel (340 V for 1–2 hours). The gel is then exposed to an X-ray film for 3–18 hours and the positive samples are identified by the presence of a band corresponding to the fragment of 11 nucleotides at the 5' end of the oligonucleotide TB-9, produced by the cleavage of TB-9 by the restriction enzyme.

EXAMPLE 5

Synthesis of the oligonucleotides according to the invention.

The oligonucleotides are synthesized using the phosphoramidite method (BEAUCAGE, 1985, loc.cit.) with a 380 D DNA synthesiser (APPLIED BIOSYSTEMS, Calif.).

TB-1, TB-2, TB-3, TB-4, TB-5, TB-6, TB-7, TB-8 and TB-9 are thereby obtained.

EXAMPLE 6

Detection of amplified sequences of MAIP group by the oligonucleotide restriction test.

The protocol is identical to that of Example 4; however, a number of reagents are different:

the oligonucleotide TB-5 is used;
the 10× buffer contains 500 mM Tris-HCl pH 8.0, 100 mM $MgCl_2$ and 400 mM NaCl;
the restriction enzyme used is BglI (10 units).

As in Example 4, the positive samples are identified by the presence of a band corresponding to a fragment of 9 nucleotides resulting from cleavage of the oligonucleotide TB-5 by the restriction enzyme BglI.

FIG. 5 shows the detection of amplified mycobacterial DNA sequences by the oligonucleotide restriction test.

The purified mycobacterial DNA is amplified, and equivalent amounts of the amplified product from *M. avium* (column 1–5), *M. bovis* BCG (column 6) and *M. fortuitum* (column 7) are evaluated as described above, using the oligonucleotide TB-5 labelled with $^{32}P$ and the restriction enzyme BglI. An amount of enzyme corresponding to the following enzymatic activities is added: 1 unit (samples 1, 6 and 7); 5 units (sample 2); 10 units (sample 3); 20 units (sample 4); and 50 units (sample 5).

The autoradiogram is exposed for 3 hours with a single intensification screen. FIG. 5 shows clearly that only columns 1–5 enable the cleaved oligomer to be demonstrated, hence permitting identification of *M. avium*.

EXAMPLE 7

Detection of mycobacterial DNA in a sputum specimen.

DNA purified from *M. tuberculosis* (FIG. 6, T), from *M. avium* (FIG. 6, A) and from *M. fortuitum* (FIG. 6, F) and DNA extracted from sputum samples which yielded a negative culture (FIG. 6, columns 1–6) or from sputum samples which yielded a positive culture for *M. tuberculosis* (FIG. 6, columns 7 and 8) was amplified using Taq polymerase in the case of the PCR or using another polymerase and the oligonucleotides TB-1 and TB-2. Samples of the amplified sequences are bound to filters (dot blots) and hybridised with the oligonucleotides TB-4, TB-5 and TB-6 labelled at their 5' end with $^{32}P$.

It is seen that the DNA of *M. tuberculosis* hybridises with TB-4.

As is apparent from the foregoing, the invention is in no way limited to those of its methods of implementation, embodiments and methods of use which have just been described more explicitly; on the contrary, it encompasses all variants which may occur to the specialist in the field without departing from the scope or range of the present invention.

We claim:

1. Peptide characterised in that it corresponds to the formula (XXI) (SEQ ID NO: 21) below:

TYR-GLU-LYS-ILE-GLY-ALA-GLU-LEU-VAL-LYS-GLU-VAL-ALA-LYS-LYS-THR-ASP-ASP-VAL-ALA-GLY-ASP-GLY-THR-THR-THR-ALA-THR-VAL-LEU-ALA-GLN-ALA-LEU-VAL-ARG-GLU-GLY-LEU-ARG-ASN-VAL-ALA-ALA-GLY-ALA-ASN-PRO-LEU-GLY-LEU-LYS-ARG-GLY-ILE-GLU-LYS-ALA-VAL-GLU-LYS-VAL-THR-GLU-THR-LEU-LEU-LYS-SER

-ALA-LYS-GLU-VAL-GLU-THR-LYS-GLU-GLN-ILE-ALA-ALA-THR-ALA-GLY-ILE-SER-ALA-GLY-ASP-GLN-SER-ILE-GLY-ASP-LEU-ILE-ALA-GLU-ALA-MET-ASP-LYS-VAL-GLY-ASN-GLU-GLY-VAL-ILE-THR-VAL-GLU-GLU-SER.                                                         (XXI)

2. Peptide characterised in that it corresponds to the formula (XXII) (SEQ ID NO: 22) below:

TYR-GLU-LYS-ILE-GLY-ALA-GLU-LEU-VAL-LYS-GLU-VAL-ALA-LYS-LYS-THR-ASP-ASP-VAL-ALA-GLY-ASP-GLY-THR-THR-THR-ALA-THR-VAL-LEU-ALA-GLN-ALA-LEU-VAL-ARG-GLU-GLY-LEU-ARG-ASN-VAL-ALA-ALA-GLY-ALA-ASN-PRO-LEU-GLY-LEU-LYS-ARG-GLY-ILE-GLU-LYS-ALA-VAL-GLU-LYS-VAL-THR-GLU-THR-LEU-LEU-LYS-SER

-ALA-LYS-GLU-VAL-GLU-THR-LYS-ASP-GLN-ILE-ALA-ALA-THR-ALA-ALA-ILE-SER-ALA-GLY-ASP-GLN-SER-ILE-GLY-ASP-LEU-ILE-ALA-GLU-ALA-MET-ASP-LYS-VAL-GLY-ASN-GLU-GLY-VAL-ILE-THR-VAL-GLU-GLU-SER.                                                        (XXII)

3. Peptide characterised in that it and corresponds to the formula (XXIII) (SEQ ID NO: 23) below:

TYR-GLU-LYS-ILE-GLY-ALA-GLU-LEU-VAL-GLU-GLU-VAL-ALA-LYS-LYS-THR-ASP-ASP-VAL-ALA-GLY-ASP-GLY-THR-THR-THR-ALA-THR-VAL-LEU-ALA-GLN-ALA-LEU-VAL-LYS-GLU-GLY-LEU-ARG-ASN-VAL-ALA-ALA-GLY-ALA-ASN-PRO-LEU-GLY-LEU-LYS-ARG-GLY-ILE-GLU-LYS-ALA-VAL-GLU-LYS-VAL-THR-GLU-THR-LEU-LEU-LYS-GLY

-ALA-LYS-GLU-VAL-GLU-THR-LYS-GLU-GLN-ILE-ALA-ALA-THR-ALA-ALA-ILE-SER-ALA-GLY-ASP-GLN-SER-ILE-GLY-ASP-LEU-ILE-ALA-ASP-GLY-MET-ASP-LYS-VAL-GLY-ASN-GLU-GLY-VAL-ILE-THR-SER-GLY-GLU-SER.                                                        (XXIII)

4. Peptide characterised in that it and corresponds to the formula (XXIV) (SEQ ID NO: 24) below:

TYR-GLU-LYS-ILE-GLY-ALA-GLU-LEU-VAL-LYS-GLU-VAL-ALA-LYS-LYS-THR-ASP-ASP-VAL-ALA-GLY-ASP-ARG-THR-THR-THR-ALA-THR-VAL-LEU-VAL-GLN-ALA-LEU-VAL-LYS-GLU-GLY-LEU-ARG-ASN-VAL-ALA-ALA-GLY-ALA-ASN-LEU-LEU-SER-PHE-LYS-CYS-GLY-ILE-GLU-LYS-ALA-VAL-GLY-LYS-VAL-THR-GLU-THR-LEU-LEU-LYS-PRO

-ALA-LYS-GLU-VAL-GLU-THR-LYS-GLU-GLN-ILE-ALA-ALA-THR-ALA-VAL-ILE-SER-VAL-GLY-ASP-GLN-SER-ILE-GLY-ASP-LEU-ILE-ALA-GLU-ALA-MET-ASP-LYS-VAL-GLY-ASN-GLU-GLY-VAL-ILE-THR-VAL-GLU-GLU-SER.                                                        (XXIV)

5. Peptide characterised in that it and corresponds to the formula (XXV) (SEQ ID NO: 25) below:

ASP-PRO-TYR-GLU-LYS-ILE-GLY-ALA-GLU-LEU-VAL-LYS-GLU-VAL-ALA-LYS-LYS-THR-ASP-ASP-VAL-ALA-GLY-ASP-ARG-THR-THR-THR-ALA-THR-VAL-LEU-ALA-GLN-ALA-LEU-VAL-LYS-GLU-GLY-LEU-ARG-ASN-VAL-ALA-ALA-GLY-ALA-ASN-PRO-LEU-GLY-LEU-LYS-ARG-GLY-ILE-GLU-LYS-ALA-VAL-GLU-LYS-VAL-THR-GLU-THR-LEU-LEU

-LYS-SER-ALA-LYS-GLU-VAL-GLU-THR-LYS-GLU-GLN-ILE-ALA-ALA-THR-ALA-ALA-ILE-SER-ALA-GLY-ASP-GLN-SER-ILE-GLY-ASP-PRO-ILE-VAL-GLU-ALA-MET-ASP-LYS-VAL-GLY-ASN-GLU-GLY-VAL-ILE-THR-VAL-GLU-GLU-SER-ASN-THR-PHE-GLY-LEU-GLN.                        (XXV)

6. Peptide characterised in that it and corresponds to the formula (XXVI) (SEQ ID NO: 26) below:

TYR-GLU-LYS-ILE-GLY-ALA-GLU-LEU-VAL-LYS-GLU-VAL-ALA-LYS-LYS-THR-ASP-ASP-VAL-ALA-ALA-ASP-GLY-THR-THR-THR-ALA-THR-VAL-LEU-ALA-GLN-ARG-LEU-VAL-ARG-GLU-GLY-LEU-ARG-ASN-VAL-ALA-ALA-GLY-ALA-ASN-PRO-LEU-GLY-LEU-LYS-ARG-GLY-ILE-GLU-LYS-ALA-VAL-GLU-ALA-VAL-THR-ALA-LYS-LEU-LEU-ASP-THR

-ALA-LYS-GLU-VAL-GLU-THR-LYS-GLU-GLN-ILE-ALA-ALA-THR-ALA-GLY-ILE-SER-ALA-GLY-ASP-ALA-SER-ILE-GLY-GLU-LEU-ILE-ALA-GLU-ALA-MET-ASP-LYS-VAL-GLY-LYS-GLU-GLY-VAL-ILE-THR-VAL-GLU-GLU-SER.                                                         (XXVI)

7. An immunogenic composition comprising the peptide according to claim 1.

8. The immunogenic composition of claim 7 further comprising at least one pharmaceutically acceptable vehicle.

9. An immunogenic composition comprising the peptide according to claim 2.

10. The immunogenic composition of claim 9 further comprising at least one pharmaceutically acceptable vehicle.

11. An immunogenic composition comprising the peptide according to claim 3.

12. The immunogenic composition of claim 11 further comprising at least one pharmaceutically acceptable vehicle.

13. An immunogenic composition comprising the peptide according to claim 4.

14. The immunogenic composition of claim 13 further comprising at least one pharmaceutically acceptable vehicle.

15. An immunogenic composition comprising the peptide according to claim 5.

16. The immunogenic composition of claim 15 further comprising at least one pharmaceutically acceptable vehicle.

17. An immunogenic composition comprising at least one according to claim 6.

18. The immunogenic composition of claim 17 further comprising at least one pharmaceutically acceptable vehicle.

19. A polyclonal or monoclonal antibody obtained by immunization of an animal with a peptide according to claim 1.

20. A polyclonal or monoclonal antibody obtained by immunization of an animal with a peptide according to claim 2.

21. A polyclonal or monoclonal antibody obtained by immunization of an animal with a peptide according to claim 3.

22. A polyclonal or monoclonal antibody obtained by immunization of an animal with a peptide according to claim 4.

23. A polyclonal or monoclonal antibody obtained by immunization of an animal with a peptide according to claim 5.

24. A polyclonal or monoclonal antibody obtained by immunization of an animal with a peptide according to claim 6.

25. A polypeptide having an amino acid sequence of the following formula (SEQ ID NO: 1):

$X_1$-TYR-GLU-LYS-ILE-GLY-ALA-GLU-LEU-VAL-$X_2$-GLU-VAL-ALA-LYS-LYS-THR-ASP-ASP-VAL-ALA-$X_3$-ASP-$X_4$-THR-THR-THR-ALA-THR-VAL-LEU-$X_5$-GLN-$X_6$-LEU-VAL-$X_7$-GLU-GLY-LEU-

ARG-ASN-VAL-ALA-ALA-GLY-ALA-ASN-$X_8$-LEU-$X_9$-$X_{10}$-LYS-$X_{11}$-GLY-ILE-GLU-LYS-ALA-VAL-GLU-$X_{12}$-VAL-THR-$X_{13}$-$X_{14}$-LEU-LEU-$X_{15}$-$X_{16}$-ALA-LYS-GLU-VAL-GLU-THR-LYS-$X_{17}$-GLN-ILE-ALA-ALA-THR-ALA-$X_{18}$-ILE-SER-$X_{19}$-GLY-ASP-$X_{20}$-SER-ILE-GLY-$X_{21}$-$X_{22}$-ILE-$X_{23}$-$X_{24}$-$X_{25}$-MET-ASP-LYS-VAL-GLY-$X_{26}$-GLU-GLY-VAL-ILE-THR-$X_{27}$-$X_{28}$-GLU-SER-$X_{29}$ in which:

$X_1$ is non-existent or represents the sequence ASP-PRO, $X_2$ represents LYS or GLU, $X_3$ represents GLY or ALA, $X_4$ represents GLY or ARG, $X_5$ represents ALA or VAL, $X_6$ represents ALA or ARG, $X_7$ represents ARG or LYS, $X_8$ represents PRO or LEU, $X_9$ represents GLY or SER, $X_{10}$ represents LEU or PHE, $X_{11}$ represents ARG or CYS, $X_{12}$ represents LYS or ALA, $X_{13}$ represents GLU or ALA, $X_{14}$ represents THR or LYS, $X_{15}$ represents LYS or ASP, $X_{16}$ represents SER, GLY, PRO or THR $X_{17}$ represents ASP or GLU, $X_{18}$ represents ALA, GLY or VAL, $X_{19}$ represents ALA or VAL, $X_{20}$ represents GLN or ALA, $X_{21}$ represents ASP or GLU, $X_{22}$ represents LEU or PRO, $X_{23}$ represents ALA or VAL, $X_{24}$ represents GLU or ASP, $X_{25}$ represents ALA or GLY, $X_{26}$ represents ASN or LYS, $X_{27}$ represents VAL or SER, $X_{28}$ represents GLU or GLY, $X_{29}$ is non-existent or represents the sequence ASN-THR-PHE-GLY-LEU-GLN.

26. An immunogenic composition comprising the polypeptide according to claim 25.

27. A polyclonal or monoclonal antibody obtained by immunization of an animal with a polypeptide according to claim 25.

* * * * *

SEQUENCE LISTING ( 1 ) GENERAL INFORMATION:

( i i i ) NUMBER OF SEQUENCES: 31

( 2 ) INFORMATION FOR SEQ ID NO:1:

( i ) SEQUENCE CHARACTERISTICS:
        ( A ) LENGTH: 116 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Xaa  Tyr  Glu  Lys  Ile  Gly  Ala  Glu  Leu  Val  Xaa  Glu  Val  Ala  Lys  Lys
  1                  5                           10                          15

Thr  Asp  Asp  Val  Ala  Xaa  Asp  Xaa  Thr  Thr  Thr  Ala  Thr  Val  Leu  Xaa
                20                          25                  30

Gln  Xaa  Leu  Val  Xaa  Glu  Gly  Leu  Arg  Asn  Val  Ala  Ala  Gly  Ala  Asn
          35                          40                          45

Xaa  Leu  Xaa  Xaa  Lys  Xaa  Gly  Ile  Glu  Lys  Ala  Val  Glu  Xaa  Val  Thr
          50                          55                  60

Xaa  Xaa  Leu  Leu  Xaa  Xaa  Ala  Lys  Glu  Val  Glu  Thr  Lys  Xaa  Gln  Ile
 65                          70                  75                          80
```

```
        Ala  Ala  Thr  Ala  Xaa  Ile  Ser  Xaa  Gly  Asp  Xaa  Ser  Ile  Gly  Xaa  Xaa
                            85                      90                      95

Ile  Xaa  Xaa  Xaa  Met  Asp  Lys  Val  Gly  Xaa  Glu  Gly  Val  Ile  Thr  Xaa
                       100                      105                     110

Xaa  Glu  Ser  Xaa
                       115
```

( 2 ) INFORMATION FOR SEQ ID NO:2:

( i ) SEQUENCE CHARACTERISTICS:
        ( A ) LENGTH: 343 base pairs
        ( B ) TYPE: nucleic acid
        ( C ) STRANDEDNESS: both
        ( D ) TOPOLOGY: linear ( i i ) MOLECULE TYPE: cDNA ( x i ) SEQUENCE DESCRIPTION: SEQ ID NO:2:

```
GTACGAGAAG  ATCGGCGCTG  AGCTCGTCAA  GGAAGTCGCC  AAGAAGACCG  ACGACGTCGC        60

GGGCGACGGC  ACCACCACCG  CCACCGTTCT  GGCACAGGCC  CTGGTTCGTG  AAGGTCTGCG       120

CAACGTCGCT  GCCGGCGCCA  ACCCGCTCGG  CCTGAAGCGC  GGCATCGAGA  AGGCCGTCGA       180

GAAGGTCACC  GAGACGCTGC  TGAAGAGCGC  CAAGGAGGTG  GAGACCAAGG  AGCAGATCGC       240

TGCCACCGCC  GGTATCTCCG  CCGGTGACCA  GTCCATCGGT  GACCTGATCG  CCGAGGCCAT       300

GGACAAGGTC  GGCAACGAGG  GTGTCATCAC  CGTCGAGGAG  AGC                         343
```

( 2 ) INFORMATION FOR SEQ ID NO:3:

( i ) SEQUENCE CHARACTERISTICS:
        ( A ) LENGTH: 343 base pairs
        ( B ) TYPE: nucleic acid
        ( C ) STRANDEDNESS: both
        ( D ) TOPOLOGY: linear ( i i ) MOLECULE TYPE: cDNA ( x i ) SEQUENCE DESCRIPTION: SEQ ID NO:3:

```
GTACGAGAAG  ATCGGCGCCG  AGCTGGTCAA  GGAAGTCGCC  AAGAAGACCG  ACGACGTCGC        60

CGGTGACGGC  ACGACGACGG  CCACGGTGCT  CGCCCAGGCG  TTGGTCCGCG  AGGGCCTGCG       120

CAACGTCGCG  GCCGGCGCCA  ACCCGCTGGG  TCTCAAGCGC  GGCATCGAGA  AGGCCGTCGA       180

GAAGGTCACC  GAGACCCTGC  TCAAGTCGGC  CAAGGAGGTC  GAGACCAAGG  ACCAGATCGC       240

TGCCACCGCG  GCCATCTCCG  CGGGCGACCA  GTCGATCGGC  GACCTGATCG  CCGAGGCGAT       300

GGACAAGGTC  GGCAACGAGG  GCGTCATCAC  CGTCGAGGAG  TCC                         343
```

( 2 ) INFORMATION FOR SEQ ID NO:4:

( i ) SEQUENCE CHARACTERISTICS:
        ( A ) LENGTH: 343 base pairs
        ( B ) TYPE: nucleic acid
        ( C ) STRANDEDNESS: both
        ( D ) TOPOLOGY: linear ( i i ) MOLECULE TYPE: cDNA ( x i ) SEQUENCE DESCRIPTION: SEQ ID NO:4:

```
GTACGAGAAG  ATCGGCGCCG  AGCTGGTCAA  AGAGGTAGCC  AAGAAGACCG  ATGACGTCGC        60

CGGTGACGGC  ACCACGACGG  CCACCGTGCT  GGCCCAGGCG  TTGGTTCGCG  AGGGCCTGCG       120

CAACGTCGCG  GCCGGCGCCA  ACCCGCTCGG  TCTCAAACGC  GGCATCGAAA  AGGCCGTGGA       180

GAAGGTCACC  GAGACCCTGC  TCAAGGGCGC  CAAGGAGGTC  GAGACCAAGG  AGCAGATTGC       240
```

```
GGCCACCGCA   GCGATTTCGG   CGGGTGACCA   GTCCATCGGT   GACCTGATCG   CCGAGGCGAT         300

GGACAAGGTG   GGCAACGAGG   GCGTCATCAC   CGTCGAGGAG   TCC                             343
```

( 2 ) INFORMATION FOR SEQ ID NO:5:

( i ) SEQUENCE CHARACTERISTICS:
    ( A ) LENGTH: 343 base pairs
    ( B ) TYPE: nucleic acid
    ( C ) STRANDEDNESS: both
    ( D ) TOPOLOGY: linear ( i i ) MOLECULE TYPE: cDNA ( x i ) SEQUENCE DESCRIPTION: SEQ ID NO:5:

```
GTACGAGAAG   ATCGGCGCCG   AGCTGGTCGA   GGAAGTCGCC   AAGAAGACCG   ACGACGTCGC         60

CGGCGACGGC   ACCACCACGG   CCACTGTGCT   CGCGCAGGCG   TTGGTCAAAG   AGGGCCTGCG         120

CAACGTCGCG   GCCGGCGCCA   ACCCACTGGG   CCTGAAGCGC   GGCATCGAGA   AGGCAGTCGA         180

GAAGGTCACC   GAGACGCTGC   TCAAGGGCGC   CAAGGAGGTC   GAGACCAAGG   AGCAGATCGC         240

TGCCACCGCG   GCCATCTCCG   CCGGTGACCA   GTCGATCGGC   GACCTGATCG   CCGATGGCAT         300

GGACAAGGTC   GGCAACGAGG   GTGTCATCAC   CGTTGAGGAG   TCC                             343
```

( 2 ) INFORMATION FOR SEQ ID NO:6:

( i ) SEQUENCE CHARACTERISTICS:
    ( A ) LENGTH: 343 base pairs
    ( B ) TYPE: nucleic acid
    ( C ) STRANDEDNESS: both
    ( D ) TOPOLOGY: linear ( i i ) MOLECULE TYPE: cDNA ( x i ) SEQUENCE DESCRIPTION: SEQ ID NO:6:

```
CTACGAGAAG   ATCGGCGCCG   AGCTGGTCAA   GGAAGTCGCC   AAGAAGACCG   ACGACGTGGC         60

CGGTGACCGG   ACGACGACGG   CCACCGTGCT   GGTGCAGGCG   CTGGTCAAAG   AGGGCCTGCG         120

CAACGTCGCG   GCCGGTGCCA   ACCTGCTCAG   CTTCAAGTGC   GGCATCGAGA   AGGCGGTCGA         180

GAAGGTCACC   GAGACCCTGC   TCAAGCCGGC   CAAGGAGGTC   GAGACCAAGG   AGCAGATCGC         240

CGCGACCGCC   GTGATCTCGG   TGGGCGACCA   GTCGATCGGT   GACCTGATCG   CCGAGGCGAT         300

GGACAAGGTT   GGCAACGAGG   GCGTCATCAC   CGTCGAGGAG   TCC                             343
```

( 2 ) INFORMATION FOR SEQ ID NO:7:

( i ) SEQUENCE CHARACTERISTICS:
    ( A ) LENGTH: 343 base pairs
    ( B ) TYPE: nucleic acid
    ( C ) STRANDEDNESS: both
    ( D ) TOPOLOGY: linear ( i i ) MOLECULE TYPE: cDNA ( x i ) SEQUENCE DESCRIPTION: SEQ ID NO:7:

```
CTACGAGAAG   ATCGGCGCCG   AGCTGGTCAA   AGAGGTCGCC   AAGAAGACCG   ACGATGTCGC         60

CGGTGACCGG   ACCACCACGG   CCACCGTGCT   GGCACAGGCG   CTGGTCAAGG   AAGGCCTGCG         120

CAACGTTGCG   GCCGGTGCCA   ACCCGCTCGG   TCTGAAGCGC   GGCATTGAGA   AGGCAGTCGA         180

GAAGGTCACC   GAGACCTTGC   TCAAGTCGGC   CAAAGAGGTC   GAGACCAAGG   AGCAGATCGC         240

GGCGACCGCA   GCCATCTCCG   CCGGCGACCA   GTCGATCGGC   GACCCGATCG   TCGAGGCGAT         300

GGACAAGGTC   GGCAACGAGG   GCGTCATTAC   CGTCGAGGAG   TCC                             343
```

( 2 ) INFORMATION FOR SEQ ID NO:8:

( i ) SEQUENCE CHARACTERISTICS:
        ( A ) LENGTH: 343 base pairs
        ( B ) TYPE: nucleic acid
        ( C ) STRANDEDNESS: both
        ( D ) TOPOLOGY: linear ( i i ) MOLECULE TYPE: cDNA ( x i ) SEQUENCE DESCRIPTION: SEQ ID NO:8:

```
CTACGAGAAG  ATCGGCGCCG  AGCTGGTCAA  GGAAGTCGCC  AAGAAGACCG  ACGACGTCGC      60
GGCTGACGGC  ACCACCACCG  CCACCGTGCT  CGCCCAGCGG  CTGGTGCGCG  AGGGTCTGCG     120
CAACGTGGCC  GCGGGCGCGA  ACCCGCTGGG  CCTCAAGCGC  GGCATCGAGA  AGGCCGTCGA     180
GGCCGTGACC  GCCAAGCTGC  TCGACACCGC  CAAGGAGGTC  GAGACCAAGG  AGCAGATCGC     240
CGCCACCGCG  GGCATCTCCG  CGGGCGACGC  GTCCATCGGT  GAGCTGATCG  CCGAGGCCAT     300
GGACAAGGTC  GGCAAGGAAG  GCGTCATCAC  CGTCGAGGAG  AGC                        343
```

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

```
GAGATCGAGC  TGGAGGATCC                                                      20
```

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:10:

```
AGCTGCAGCC  CAAAGGTGTT                                                      20
```

( 2 ) INFORMATION FOR SEQ ID NO:11:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

```
GCGGCATCGA  AAAGGCCGTG                                                      20
```

( 2 ) INFORMATION FOR SEQ ID NO:12:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

CGAAATCGCT GCGGTGGCCG 20

( 2 ) INFORMATION FOR SEQ ID NO:13:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:13:

CTGCCACCGC GGCCATCTCC 20

( 2 ) INFORMATION FOR SEQ ID NO:14:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:14:

CTGCCACCGC CGGTATCTCC 20

( 2 ) INFORMATION FOR SEQ ID NO:15:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:15:

AACGTCGCGG CCGGCGCCAA 20

( 2 ) INFORMATION FOR SEQ ID NO:16:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:16:

GACTCCTCGA CGGTGATGAC 20

( 2 ) INFORMATION FOR SEQ ID NO:17:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:17:

CCTGCTCAAG GGCGCCAAG 19

( 2 ) INFORMATION FOR SEQ ID NO:18:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:18:

CGAAATCGCT GCGGTGGCCG CAATCTGCTC        30

( 2 ) INFORMATION FOR SEQ ID NO:19:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:19:

GGTGCTCGCC CAGGCGTTGG TCCGC        25

( 2 ) INFORMATION FOR SEQ ID NO:20:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:20:

TGTGCTCGCG CAGGCGCTGG TCAAA        25

( 2 ) INFORMATION FOR SEQ ID NO:21:

( i ) SEQUENCE CHARACTERISTICS:
        ( A ) LENGTH: 114 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:21:

```
Tyr Glu Lys Ile Gly Ala Glu Leu Val Lys Glu Val Ala Lys Lys Thr
 1               5                  10                  15
Asp Asp Val Ala Gly Asp Gly Thr Thr Thr Ala Thr Val Leu Ala Gln
            20                  25                  30
Ala Leu Val Arg Glu Gly Leu Arg Asn Val Ala Ala Gly Ala Asn Pro
                35                  40                  45
Leu Gly Leu Lys Arg Gly Ile Glu Lys Ala Val Glu Lys Val Thr Glu
        50                  55                  60
Thr Leu Leu Lys Ser Ala Lys Glu Val Glu Thr Lys Glu Gln Ile Ala
65                  70                  75                  80
Ala Thr Ala Gly Ile Ser Ala Gly Asp Gln Ser Ile Gly Asp Leu Ile
                85                  90                  95
Ala Glu Ala Met Asp Lys Val Gly Asn Glu Gly Val Ile Thr Val Glu
                100                 105                 110
Glu Ser
```

( 2 ) INFORMATION FOR SEQ ID NO:22:

( i ) SEQUENCE CHARACTERISTICS:
        ( A ) LENGTH: 114 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:22:

```
Tyr Glu Lys Ile Gly Ala Glu Leu Val Lys Glu Val Ala Lys Lys Thr
  1               5                  10                  15
Asp Asp Val Ala Gly Asp Gly Thr Thr Thr Ala Thr Val Leu Ala Gln
             20                  25                  30
Ala Leu Val Arg Glu Gly Leu Arg Asn Val Ala Ala Gly Ala Asn Pro
         35                  40                  45
Leu Gly Leu Lys Arg Gly Ile Glu Lys Ala Val Glu Lys Val Thr Glu
     50                  55                  60
Thr Leu Leu Lys Ser Ala Lys Glu Val Glu Thr Lys Asp Gln Ile Ala
 65                  70                  75                  80
Ala Thr Ala Ala Ile Ser Ala Gly Asp Gln Ser Ile Gly Asp Leu Ile
                 85                  90                  95
Ala Glu Ala Met Asp Lys Val Gly Asn Glu Gly Val Ile Thr Val Glu
                100                 105                 110
Glu Ser
```

( 2 ) INFORMATION FOR SEQ ID NO:23:

( i ) SEQUENCE CHARACTERISTICS:
        ( A ) LENGTH: 114 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:23:

```
Tyr Glu Lys Ile Gly Ala Glu Leu Val Glu Val Ala Lys Lys Thr
  1               5                  10                  15
Asp Asp Val Ala Gly Asp Gly Thr Thr Thr Ala Thr Val Leu Ala Gln
             20                  25                  30
Ala Leu Val Lys Glu Gly Leu Arg Asn Val Ala Ala Gly Ala Asn Pro
         35                  40                  45
Leu Gly Leu Lys Arg Gly Ile Glu Lys Ala Val Glu Lys Val Thr Glu
     50                  55                  60
Thr Leu Leu Lys Gly Ala Lys Glu Val Glu Thr Lys Glu Gln Ile Ala
 65                  70                  75                  80
Ala Thr Ala Ala Ile Ser Ala Gly Asp Gln Ser Ile Gly Asp Leu Ile
                 85                  90                  95
Ala Asp Gly Met Asp Lys Val Gly Asn Glu Gly Val Ile Thr Ser Gly
                100                 105                 110
Glu Ser
```

( 2 ) INFORMATION FOR SEQ ID NO:24:

( i ) SEQUENCE CHARACTERISTICS:
        ( A ) LENGTH: 114 amino acids
        ( B ) TYPE: amino acid
        ( C ) STRANDEDNESS: single (D) TOPOLOGY: linear (ii) MOLECULE TYPE: peptide (xi) SEQUENCE DESCRIPTION: SEQ ID NO:24:

| Tyr | Glu | Lys | Ile | Gly | Ala | Glu | Leu | Val | Lys | Glu | Val | Ala | Lys | Lys | Thr |
|---|---|---|---|---|---|---|---|---|---|---|---|---|---|---|---|
| 1 | | | | 5 | | | | | 10 | | | | | 15 | |
| Asp | Asp | Val | Ala | Gly | Asp | Arg | Thr | Thr | Thr | Ala | Thr | Val | Leu | Val | Gln |
| | | | 20 | | | | 25 | | | | | 30 | | | |
| Ala | Leu | Val | Lys | Glu | Gly | Leu | Arg | Asn | Val | Ala | Ala | Gly | Ala | Asn | Leu |
| | | 35 | | | | | 40 | | | | | 45 | | | |
| Leu | Ser | Phe | Lys | Cys | Gly | Ile | Glu | Lys | Ala | Val | Glu | Lys | Val | Thr | Glu |
| | 50 | | | | | 55 | | | | | 60 | | | | |
| Thr | Leu | Leu | Lys | Pro | Ala | Lys | Glu | Val | Glu | Thr | Lys | Glu | Gln | Ile | Ala |
| 65 | | | | | 70 | | | | | 75 | | | | | 80 |
| Ala | Thr | Ala | Val | Ile | Ser | Val | Gly | Asp | Gln | Ser | Ile | Gly | Asp | Leu | Ile |
| | | | | 85 | | | | | 90 | | | | | 95 | |
| Ala | Glu | Ala | Met | Asp | Lys | Val | Gly | Asn | Glu | Gly | Val | Ile | Thr | Val | Glu |
| | | | 100 | | | | | 105 | | | | | 110 | | |
| Glu | Ser | | | | | | | | | | | | | | |

(2) INFORMATION FOR SEQ ID NO:25:

(i) SEQUENCE CHARACTERISTICS:
    (A) LENGTH: 122 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:25:

| Asp | Pro | Tyr | Glu | Lys | Ile | Gly | Ala | Glu | Leu | Val | Lys | Glu | Val | Ala | Lys |
|---|---|---|---|---|---|---|---|---|---|---|---|---|---|---|---|
| 1 | | | | 5 | | | | | 10 | | | | | 15 | |
| Lys | Thr | Asp | Asp | Val | Ala | Gly | Asp | Arg | Thr | Thr | Thr | Ala | Thr | Val | Leu |
| | | | 20 | | | | 25 | | | | | 30 | | | |
| Ala | Gln | Ala | Leu | Val | Lys | Glu | Gly | Leu | Arg | Asn | Val | Ala | Ala | Gly | Ala |
| | | 35 | | | | | 40 | | | | | 45 | | | |
| Asn | Pro | Leu | Gly | Leu | Lys | Arg | Gly | Ile | Glu | Lys | Ala | Val | Glu | Lys | Val |
| | 50 | | | | | 55 | | | | | 60 | | | | |
| Thr | Glu | Thr | Leu | Leu | Lys | Ser | Ala | Lys | Glu | Val | Glu | Thr | Lys | Glu | Gln |
| 65 | | | | | 70 | | | | | 75 | | | | | 80 |
| Ile | Ala | Ala | Thr | Ala | Ala | Ile | Ser | Ala | Gly | Asp | Gln | Ser | Ile | Gly | Asp |
| | | | | 85 | | | | | 90 | | | | | 95 | |
| Pro | Ile | Val | Glu | Ala | Met | Asp | Lys | Val | Gly | Asn | Glu | Gly | Val | Ile | Thr |
| | | | 100 | | | | | 105 | | | | | 110 | | |
| Val | Glu | Glu | Ser | Asn | Thr | Phe | Gly | Leu | Gln | | | | | | |
| | | 115 | | | | | 120 | | | | | | | | |

(2) INFORMATION FOR SEQ ID NO:26:

(i) SEQUENCE CHARACTERISTICS:
    (A) LENGTH: 114 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:26:

| Tyr | Glu | Lys | Ile | Gly | Ala | Glu | Leu | Val | Lys | Glu | Val | Ala | Lys | Lys | Thr |
|---|---|---|---|---|---|---|---|---|---|---|---|---|---|---|---|

|     | 1   |     |     |     | 5   |     |     |     |     | 10  |     |     |     |     | 15  |
| --- | --- | --- | --- | --- | --- | --- | --- | --- | --- | --- | --- | --- | --- | --- | --- |

Asp Asp Val Ala Ala Asp Gly Thr Thr Ala Thr Val Leu Ala Gln
            20                  25                  30

Arg Leu Val Arg Glu Gly Leu Arg Asn Val Ala Ala Gly Ala Asn Pro
            35                  40                  45

Leu Gly Leu Lys Arg Gly Ile Glu Lys Ala Val Glu Ala Val Thr Ala
            50                  55                  60

Lys Leu Leu Asp Thr Ala Lys Glu Val Glu Thr Lys Glu Gln Ile Ala
65                  70                  75                  80

Ala Thr Ala Gly Ile Ser Ala Gly Asp Ala Ser Ile Gly Glu Leu Ile
                85                  90                  95

Ala Glu Ala Met Asp Lys Val Gly Lys Glu Gly Val Ile Thr Val Glu
            100                 105                 110

Glu Ser ( 2 ) INFORMATION FOR SEQ ID NO:27:

( i ) SEQUENCE CHARACTERISTICS:
        ( A ) LENGTH: 114 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:27:

Tyr Glu Lys Ile Gly Ala Glu Leu Val Lys Glu Val Ala Lys Lys Thr
1                   5                   10                  15

Asp Asp Val Ala Gly Asp Gly Thr Thr Thr Ala Thr Val Leu Ala Gln
            20                  25                  30

Ala Leu Val Arg Glu Gly Leu Arg Asn Val Ala Ala Gly Ala Asn Pro
            35                  40                  45

Leu Gly Leu Lys Arg Gly Ile Glu Lys Ala Val Glu Lys Val Thr Glu
            50                  55                  60

Thr Leu Leu Lys Gly Ala Lys Glu Val Glu Thr Lys Glu Gln Ile Ala
65                  70                  75                  80

Ala Thr Ala Ala Ile Ser Ala Gly Asp Gln Ser Ile Gly Asp Leu Ile
                85                  90                  95

Ala Glu Ala Met Asp Lys Val Gly Asn Glu Gly Val Ile Thr Val Glu
            100                 105                 110

Glu Ser ( 2 ) INFORMATION FOR SEQ ID NO:28:

( i ) SEQUENCE CHARACTERISTICS:
        ( A ) LENGTH: 342 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:28:

```
TACGAGAAGA TCGGCGCCGA GCTGGTCAAG GAAGTCGCCA AGAAGACCGA CGACGTCGCC      60
GGTGACGGCA CGACGACGGC CACGGTGCTC CCCCAGGCGT TGGTCCGCGA GGGCCTGCGC     120
AACGTCGCGG CCGGCGCCAA CCCGCTGGGT CTCAAGCGCG GCATCGAGAA GGCCGTCGAG     180
AAGGTCACCG ACACCCTGCT CAAGTCGGCC AAGGAGGTCG AGACCAAGGA CCAGATCGCT     240
GCCACCGCGG CCATCTCCGC GGGCGACCAG TCGATCGGCG ACCTGATCGC CGAGGCGATG     300
```

GACAAGGTCG GCAACGAGGG CGTCATCACC GTCGAGGAGT CC 342

(2) INFORMATION FOR SEQ ID NO:29:

(i) SEQUENCE CHARACTERISTICS:
    (A) LENGTH: 342 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:29:

TACGAGAAGA TCGGCGCTGA GCTCGTCAAG GAAGTCGCCA AGAAGACCGA CGACGTCGCG 60
GGCGACGGCA CCACCACCGC CACCGTTCTG GCACAGGCCC TGGTTCGTGA AGGTCTGCGC 120
AACGTCGCTG CCGGCGCCAA CCCGCTCGGC CTGAAGCGCG GCATCGAGAA GCCCGTCGAG 180
AAGGTCACCG AGACGCTGCT GAAGAGCGCC AAGGAGGTGG AGACCAAGGA GCAGATCGCT 240
GCCACCGCCG GTATCTCCGC CGGTGACCAG TCCATCGGTG ACCTGATCCC CGAGGCCATG 300
GACAAGGTCG GCAACGAGGG TGTCATCACC GTCGAGGAGA GC 342

(2) INFORMATION FOR SEQ ID NO:30:

(i) SEQUENCE CHARACTERISTICS:
    (A) LENGTH: 342 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:30:

TACGAGAAGA TCGGCGCCGA GCTGGTCAAG GAAGTCGCCA AGAAGACCGA CGACGTCGCC 60
GGTGACGGCA CGACGACGGC CACGGTCCTC GCCCAGGCGT TGGTCCGCGA GGGCCTGCGC 120
AACGTCGCGG CCGGCGCCAA CCCGCTGGGT CTCAAGCGCG GCATCGAGAA GGCCGTCGAG 180
AAGGTCACCG AGACCCTGCT CAAGTCGGCC AAGGAGGTCG AGACCAAGGA CCAGATCGCT 240
GCCACCGCGG CCATCTCCGC GGGCGACCAG TCGATCGGCG ACCTGATCGC CGAGGCGATG 300
GACAAGGTCG GCAACGAGGG CGTCATCACC GTCGAGGAGT CC 342

(2) INFORMATION FOR SEQ ID NO:31:

(i) SEQUENCE CHARACTERISTICS:
    (A) LENGTH: 342 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:31:

TACGAGAAGA TCGGCGCCGA GCTGGTCAAA GAGGTAGCCA AGAAGACCGA TGACGTCGCC 60
GGTGACGGCA CCACGACGGC CACCGTGCTG GCCCAGGCGT TGGTTCGCGA GGGCCTGCGC 120
AACGTCGCGG CCGGCGCCAA CCCGCTCGGT CTCAAACGCG GCATCGAAAA GGCCGTGGAG 180
AAGGTCACCG AGACCCTGCT CAAGGGCGCC AAGGAGGTCG AGACCAAGGA GCAGATTGCG 240
GCCACCGCAG CGATTTCGGC GGGTGACCAG TCCATCGGTG ACCTGATCGC CGAGGCGATG 300
GACAAGGTGG GCAACGAGGG CGTCATCACC GTCGAGGAGT CC 342